(12) United States Patent
Dominguez et al.

(10) Patent No.: US 7,256,302 B2
(45) Date of Patent: Aug. 14, 2007

(54) SUBSTITUTED PARACYCLOPHANE DERIVATIVES IN ASYMMETRIC CATALYSIS

(75) Inventors: Beatriz Dominguez, Suffolk (GB); William Patrick Hems, Norfolk (GB); Antonio Zanotti-Gerosa, Cambridge (GB)

(73) Assignee: Johnson Matthey PLC, London (GB)

( * ) Notice: Subject to any disclaimer, the term of this patent is extended or adjusted under 35 U.S.C. 154(b) by 0 days.

(21) Appl. No.: 10/560,387

(22) PCT Filed: Jun. 8, 2004

(86) PCT No.: PCT/GB2004/002426

§ 371 (c)(1),
(2), (4) Date: Apr. 18, 2006

(87) PCT Pub. No.: WO2004/111065

PCT Pub. Date: Dec. 23, 2004

(65) Prior Publication Data

US 2006/0229473 A1    Oct. 12, 2006

(30) Foreign Application Priority Data

Jun. 13, 2003  (GB) ................. 0313709.8
Feb. 4, 2004   (GB) ................. 0402416.2

(51) Int. Cl.
    *C07F 9/30*          (2006.01)
(52) U.S. Cl. .......................... 556/20; 568/17
(58) Field of Classification Search ........... 556/20; 568/17
    See application file for complete search history.

(56) References Cited

U.S. PATENT DOCUMENTS

| 5,276,053 A | 1/1994 | Johnson |
| 5,874,629 A * | 2/1999 | Pye et al. ............ 568/17 |
| 6,613,922 B2 * | 9/2003 | Zanotti-Gerosa et al. ..... 556/19 |

FOREIGN PATENT DOCUMENTS

| WO | WO-97/47632 A1 | 12/1997 |
| WO | WO-01/74829 A1 | 10/2001 |
| WO | WO-02/057278 A1 | 7/2002 |
| WO | WO-02/066159 A1 | 8/2002 |

OTHER PUBLICATIONS

Glenn P. Bartholomew and Guillermo C. Bazan Synthesis, Characterization, and Spectroscopy of 4,7,12,15-[2.2]Paracyclophane Containing Donor and Acceptor Groups: Impact of Substitution Patterns on Through-Space Charge Transfer J. Am. Chem. Soc. 2002, 124, 5183-96.*

Philip J. Pye et al., "A New Planar Chiral Bisphosphine Ligand for Asymmetric Catalysis: Highly Enantioselective Hydrogenations under Mild Conditions," *J. Am Chem. Soc.*, 1997, vol. 119, pp. 6207-6208.

Beatriz Dominguez et al., "Electrophilic Substitution of Dibromoparacyclophane: A Route to Novel Paracyclophane Phosphine Ligands," *Organic Letters*, 2004, vol. 4, No. 12, pp. 1927-1930.

Glenn P. Bartholomew et al., "Synthesis, Characterization, and Spectroscopy of 4,7,12,15-[2.2]Paracyclophane Containing Donor and Acceptor Groups: Impact of Substitution Patterns on Through-Space Charge Transfer," *J. Am. Chem. Soc.*, 2002, vol. 124, pp. 5183-5196.

Andrew Pelter et al., "The synthesis of homochiral ligands based on [2.2]paracyclophane," *Tetrahedron Letters*, 2001, vol. 42, pp. 8391-8394.

Abstract: Ahmed M. Nour-El-Din et al, "Chemical reactions on thin-layer chromatoplates: Part I. Reactions of nitrones and [2.2]paracyclophanes," *Indian Journal of Chemistry, Section B: Organic Chemistry Including Medicinal Chemistry*, 1983, vol. 22B, No. 5, pp. 477-480.

Susan E. Gibson et al., "[2.2]Paracyclophane derivatives in asymmetric catalysis," *Org. Biomol. Chem.*, 2003, vol. 1, pp. 1256-1269.

Hans J. Reich et al, "Macro Rings. XXXVII. Multiple Electrophilic Substitution Reactions of [2.2]Paracyclophanes and Interconversions of Polysubstituted Derivatives," *J. Am. Chem. Soc.*, 1969, vol. 91, No. 13, pp. 3527-3533.

Antonio Zanotti-Gerosa et al. , Phosphonites Based on the Paracyclophane Backbone: New Ligands for Highly Selective Rhodium-Catalyzed Asymmetric Hydrogenation,*Organic Letters*, 2002, Vo. 3, No. 23, pp. 3687-3690.

* cited by examiner

*Primary Examiner*—Sudhakar Katakam
(74) *Attorney, Agent, or Firm*—RatnerPrestia

(57) ABSTRACT

A substituted paracyclophane is described of formula (I) wherein $X^1$ and $X^2$ are linking groups comprising between 2 to 4 carbon atoms, $Y^1$ and $Y^2$ are selected from the group consisting of hydrogen, halide, oxygen, nitrogen, alkyl, cycloalkyl, aryl or heteroaryl, $Z^1$, $Z^2$ and $Z^3$ are substituting groups that optionally contain functional groups, a, b, c, d, e and f are 0 or 1 and $a+b+c+d+e+f=1$ to 6. Preferably $X^1$ and $X^2$ are —$(C_2H_4)$— and $a+b+c+d+e+f=1$ or 2. The substituted paracyclophane provides transition metal catalysts that demonstrate high activity and selectivity for asymmetric reactions (I)

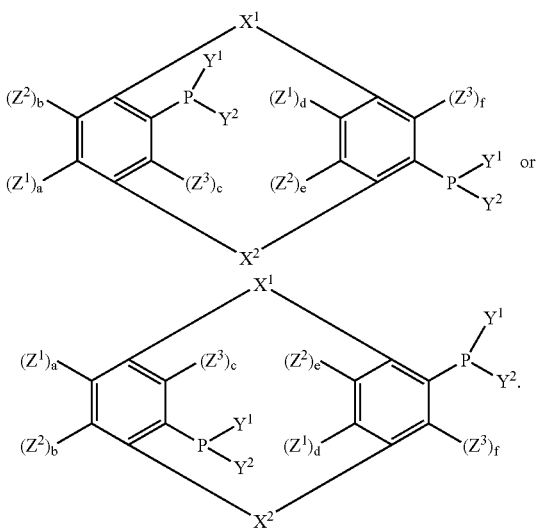

16 Claims, No Drawings

SUBSTITUTED PARACYCLOPHANE DERIVATIVES IN ASYMMETRIC CATALYSIS

This application is the U.S. National Phase application of PCT International Application No. PCT/GB2004/002426, filed Jun. 8, 2004, and claims priority of British Patent Application No. 0313709.8, filed Jun. 13, 2003, and British Patent Application No. 0402416.2, filed Feb. 4, 2004.

FIELD OF THE INVENTION

This invention relates to ligands used in transition metal-catalysed asymmetric reactions and in particular to paracyclophanes more particularly to substituted paracyclophanes.

BACKGROUND

Paracyclophanes and in particular [2.2]-paracyclophane derivatives are established ligands for transition metal-catalysed asymmetric reactions (see for example, S. E. Gibson and J. D. Knight, Org. Biomol. Chem., 2003, 1, 1256-1269). Of these, paracyclophane bis(phosphines) have attracted considerable attention because catalysts derived from them show high levels of activity and selectivity in a number of useful asymmetric transformations.

For example, WO 97/47632 describes paracyclophane bis(phosphine) ligands and rhodium (Rh), ruthenium (Ru), iridium (Ir) or palladium (Pd) catalysts derived therefrom for asymmetric hydrogenation, isomerization, hydroboration, cyclization, arylation, alkylation and amination reactions. The ligands described have the formula depicted below;

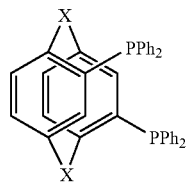

$X = -(CH_2)_n-; \quad -CH_2OCH_2-; \quad -CH_2SO_2CH_2-.$

Where both X groups are the identical, these ligands posses $C_2$ symmetry, that is they are chiral and have a $C_2$ axis of symmetry. For example, the $C_2$-symmetric [2.2] ligand where $X=-(CH_2CH_2)-$, known as PHANEPHOS, may be used in the asymmetric hydrogenation of ketones when comprising part of a Ru-diamine complex (see WO 01/74829).

WO 02/057278 describes paracyclophane ligands structurally related to the paracyclophane bis(phosphines) where the phenyl groups bound to the phosphorus in the [2.2] paracyclophane structure are replaced by oxygen, nitrogen, chloride or hydrogen atoms. These ligands are depicted below;

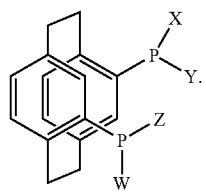

X, Y, Z, W = O; paracyclophane phosphonites
X, Y, Z, W = N; paracyclophane phosphorus-amides
X, Z = O, Y, W = N; paracyclophane phosphonamidite
X, Y, Z, W = Cl; bis(dichlorophosphino) paracyclophane
X, Y, Z, W = H; diphosphino paracyclophane Rh, Ir and Ru catalysts derived therefrom were used in asymmetric hydrogenation reactions.

Whereas the paracyclophane ligands described are effective for many asymmetric transformations there is still a need to improve the activity and selectivity of catalysts derived from them over a broader range of reactions and substrates. In addition, the paracyclophane ligands generally require lengthy and expensive resolution techniques in order to provide them in high enantiomeric purity for preparing catalysts for asymmetric transformations.

Furthermore, whereas the catalysts derived from the ligands described may be effective for providing acceptable activity and selectivity in these reactions when used as homogeneous catalysts, they are not particularly amenable to immobilisation on solid supports. The fixing of homogeneous catalysts to solid supports provides the potential for extending the benefits of heterogeneous catalysts to homogeneous systems. These benefits include easier separation of catalyst and reaction products leading to shorter work up times and improved process efficiency, the potential for re-activation and re-use of the supported catalysts which are often based on expensive metals and complex ligand geometry, and the possible adaptation of the immobilised catalyst to continuous flow fixed-bed processes.

SUMMARY OF THE INVENTION

We have found that by providing a substituting group on one or both of the benzene rings in a paracyclophane structure that electronic and/or steric properties of the ligand may be altered. Furthermore, the substituting group may also be used to facilitate chiral resolution of the paracyclophane and if desired to provide a functional group suitable for reaction with a solid support material.

Accordingly the present invention provides a substituted paracyclophane of formula (I)

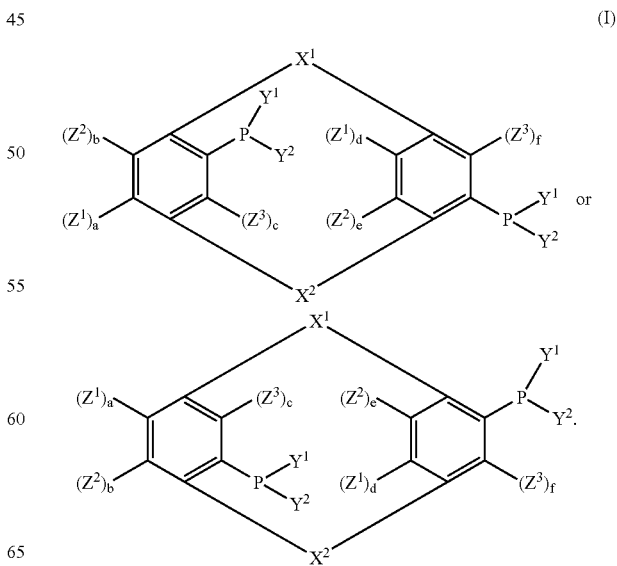

wherein $X^1$ and $X^2$ are linking groups comprising between 2 to 4 carbon atoms, $Y^1$ and $Y^2$ are selected from the group consisting of hydrogen, halide, oxygen, nitrogen, alkyl, cycloalkyl, aryl or heteroaryl, $Z^1$, $Z^2$ and $Z^3$ are substituting groups that optionally contain functional groups, wherein a, b, c, d, e and f are 0 or 1 and a+b+c+d+e+f=1 to 6.

DETAILED DESCRIPTION OF THE INVENTION

Linking groups $X^1$ and $X^2$ provide links between the benzene rings of the paracyclophane structure that comprise between 2 and 4 carbon atoms. Hence $X^1$ and $X^2$ may be linear, branched or cyclic structures where the link is formed via 2, 3 or 4 carbon atoms. The links may, in addition to the carbon atoms, contain heteroatoms such as O, N or S (where the N atom may in turn be bonded to an alkyl group such as $CH_3$, $C_2H_5$, $C_3H_7$ or $C_4H_9$ or an aryl group, and the S atom may be bonded to an alkyl or aryl group or be part of an SO or $SO_2$ moiety) and/or the carbon atoms in the linking group may be substituted with a halide, e.g. one or more fluorine atoms. Hence linking groups $X^1$ and $X^2$ may independently be for example —$(CH_2)_{2-4}$—, —$CH_2OCH_2$—, —$CH_2N(CH_3)CH_2$—, —$CH_2SO_2CH_2$—, —$C_2F_4$— or ortho, meta or para —$C_6H_4$ Such modification of the linking group may be useful for adapting the substituted paracyclophane to different reaction conditions, e.g. solvents. Preferably the linking groups comprise —$(C_2H_4)$—, —$(C_3H_6)$— or —$(C_4H_8)$—. More preferably $X^1$ and $X^2$ are the same and most preferably $X^1$ and $X^2$ are both —$(C_2H_4)$—.

In one embodiment the paracyclophane is a bis(phosphine) where $Y^1$ and $Y^2$ may independently be hydrogen, halide (Cl, Br, F or I) or straight chain or branched alkyl groups (e.g. C1-C20) such as methyl, ethyl, propyl, iso-propyl, butyl, iso-butyl, sec-butyl, tert-butyl, pentyl, hexyl, heptyl, octyl, nonyl, decyl, dodecyl, and stearyl, cycloalkyl groups (e.g. C3-C10) such as cyclopropyl, cyclobutyl, cyclopentyl, cyclohexyl or adamantyl, or aryl groups such as phenyl, naphthyl or anthracyl. The alkyl groups may be optionally substituted with one or more substituents such as halide (Cl, Br, F or I) or alkoxy groups, e.g. methoxy, ethoxy or propoxy groups. The aryl groups may be optionally substituted with one or more substituents such as halide (Cl, Br, F or I), methyl, trifluoromethyl or methoxy groups. Suitable substituted aryl groups include 4-methylphenyl, 3,5-dimethylphenyl, 4-methoxyphenyl and 4-methoxy-3,5-dimethylphenyl. Substituted or unsubstituted heteroaryl groups such as pyridyl may also be used. In an alternative embodiment, $Y^1$ and $Y^2$ on each phosphorus atom may be linked so as to form a ring structure incorporating the phosphorus atom. In such an embodiment, preferably $Y^1$ and $Y^2$ are linked so as to provide each phosphorus atom in a 4- to 7-membered ring. In yet a further embodiment, the paracyclophane may be a phosphonite (where $Y^1$ and $Y^2$ are oxygen atoms), a phosphorus-amide (where $Y^1$ and $Y^2$ are nitrogen atoms), or a phosphonamidite (where $Y^1$ is an oxygen atom and $Y^2$ is a nitrogen atom). Preferably, $Y^1$ and $Y^2$ are the same and are phenyl or substituted phenyl groups.

Substituting groups $Z^1$, $Z^2$ and $Z^3$ depending upon their number and position replace hydrogen atoms on one or both benzene rings of the paracyclophane (I). $Z^1$, $Z^2$ or $Z^3$ may independently be non-functional group-containing substituting groups such as branched or linear alkyl (e.g. C1-C30, preferably C1-C20, more preferably C1-C10 as described above for $Y^1$ and $Y^2$) or aryl (e.g. phenyl, naphthyl or anthracyl) or aralkyl or alkaryl, (e.g. benzyl, —$CH_2C_6H_5$). Such substituting groups may be effective in altering the physical, electronic and/or steric properties of the paracyclophane for example where the paracyclophane is used as part of a transition metal catalyst complex. Additionally or alternatively $Z^1$, $Z^2$ or $Z^3$ may be substituting groups that comprise one or more functional groups that may, if desired, be used to alter the electronic properties of the ligand, facilitate chiral resolution of the paracyclophane ligand or an intermediate thereof and/or covalently bond the paracyclophane ligand (or an intermediate thereof) and hence a catalyst derived therefrom, to a suitably reactive solid support. Hence substituting groups $Z^1$, $Z^2$ and $Z^3$ may optionally comprise one or more functional groups. Suitable functional groups include halide (Cl, Br, F or I), hydroxyl, alkoxy (i.e. —OR where e.g. R=alkyl C1-C30), carbonyl, carboxyl, anhydride, methacryl, epoxide, vinyl, nitrile, nitro, sulphate, sulphonyl, mercapto, sulphide amino, amine, imine, amide and imide. These functional groups may, where appropriate, be directly bonded to the benzene ring in the paracyclophane ligand or may be present in alkyl (e.g. C1-C30 as described above for $Y^1$ and $Y^2$), aryl or alkyl-aryl groups bonded to the benzene ring. In addition $Z^1$, $Z^2$ or $Z^3$ on one benzene ring in the paracyclophane structure may be the same or different from $Z^1$, $Z^2$ or $Z^3$ on the other benzene ring, i.e. $(Z^1)_a$, $(Z^2)_b$ and $(Z^3)_c$, may be the same or different from $(Z^1)_d$, $(Z^2)_e$, and $(Z^3)_f$.

Particularly preferred substituting groups are alkyl groups such as —$CH_3$(Me), —$C(CH_3)_3$(tBu), —$CH(CH_3)_2$(iPr), aryl groups such as —$C_6H_5$(Ph); fluoroalkyl groups e.g. of formula —CxHyFz (in which x is 1 to 10, preferably 1 to 3; y is less than 2x, including 0; and z=1 to 2x+1), vinyl —$CH$=$CH_2$, iodide —I, nitrate —$NO_2$, imino e.g. —N=$CPh_2$, alkoxymethylene or alkoxy groups R'$OCH_2$— or R'O— (e.g. where R'=H, alkyl C1-C30, aryl, alkaryl or silyl, especially $CH_2Ph$, $CH_3$, tBu, iPr, Si(tBu)$Me_2$ or Si(iPr)$_3$); carbonyl XC(O)— (e.g. where X=H, halide, especially Cl, alkyl C1-C30, preferably C1-C10), carboxyl R"$O_2C$— (e.g. where R"=H, alkyl C1-C30, aryl or alkaryl such as $CH_3$, Ph-$CH_2$, tBu, iPr, preferably H); and amino R'R"N—, R'R"$NCH_2$— or R'R"NCO— (e.g. where R' and/or R"=H, alkyl, or alkaryl such as $CH_3$, $CH_2Ph$).

The substituting group on each benzene ring in the paracyclophane structure may be in an ortho ($Z^3$), meta ($Z^2$) and/or para ($Z^1$) position to the P($Y^1Y^2$) group. When the substituent is at the para-position of the benzene ring it may enhance the electronic effects on the P($Y^1Y^2$) group and permits, by choice of suitable $Z^1$ substituents the possibility of electronic fine-tuning of the ligand to enhance its effect when part of a catalyst for different reactions and substrates. By careful choice of the $Z^2$ or particularly the $Z^3$ substituent in the ortho-position, the steric properties of the ligand may be altered to effect changes in catalyst selectivity. The substituting groups may also be used to alter the physical properties of the paracyclophane e.g. it's stability in air, towards water, or its solubility in different solvents. Preferably the substituting group on each benzene ring in the paracyclophane is in the para ($Z^1$) position to the P($Y^1Y^2$) group.

At least one and up to six substituting groups may be present on the substituted paracyclophane (I) of the present invention. While each benzene ring in the paracyclophane structure may comprise three substituting groups, it is preferred that each benzene ring comprises one or two substituting groups such that a+b+c+d+e+f=1 to 4, more preferably a+b+c +d+e+f=1 or 2. Most preferably each benzene ring comprises only one substituting group, i.e. a+b+c=1 and/or d+e+f=1 and particularly a and/or d=1.

Paracyclophanes of the present invention, suitable for use as ligands for the preparation of catalysts, include but are not restricted to the following;

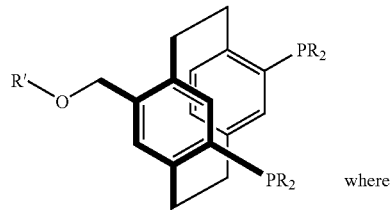

where
R = Trityl, Ph, Tol, Xyl, MeO—Xyl, MeO—Ph, i-Pr, c-Hex, t-Bu
R' = H, CH₂Ph, CH₃, t-Bu, i-Pr, Si(t-Bu)Me₂, Si(i-Pr)₃,

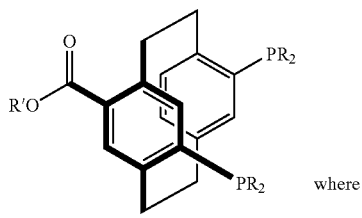

where
R = Ph, Tol, Xyl, MeO—Xyl, MeO—Ph, i-Pr, c-Hex, t-Bu
R' = H, CH₃, Ph—CH₂, t-Bu, i-Pr

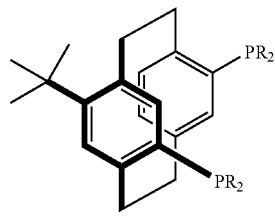

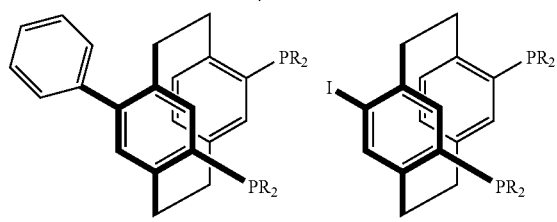

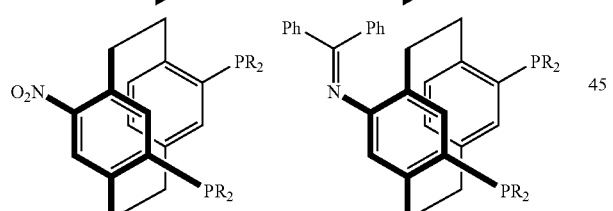

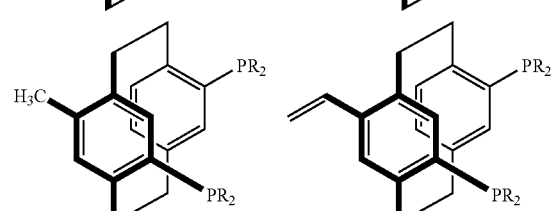

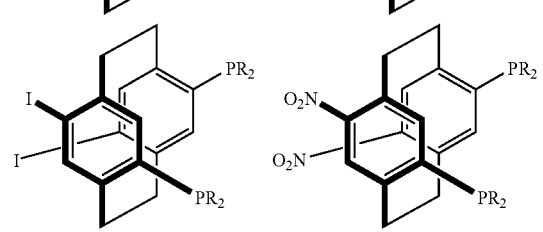

-continued

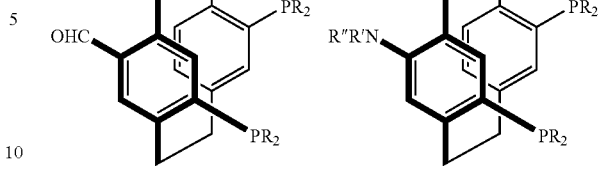

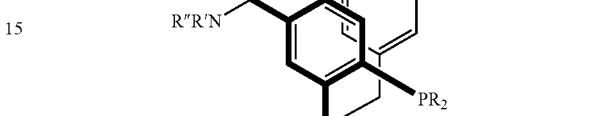

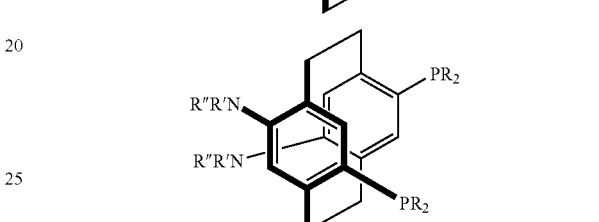

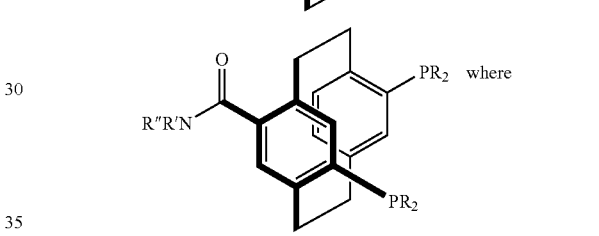

where
R = Ph, Tol, Xyl, MeO—Xyl, MeO—Ph, i-Pr, c-Hex, t-Bu
R'R''N = NH₂, NHMe, NH(CH₂Ph), NMe₂, N(CH₂Ph)₂

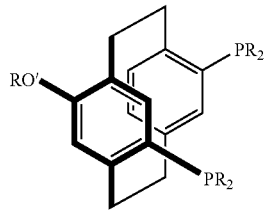

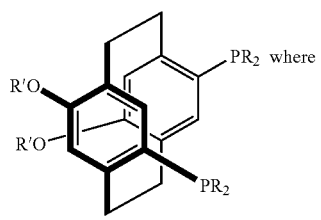

where
R = Trityl, Ph, Tol, Xyl, MeO—Xyl, MeO—Ph, i-Pr, c-Hex, t-Bu
R' = H, CH₂Ph, CH₃, t-Bu, i-Pr, Si(t-Bu)Me₂, Si(i-Pr)₃,

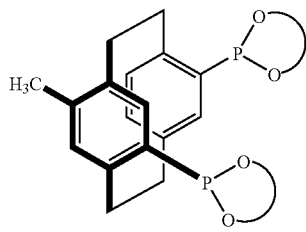

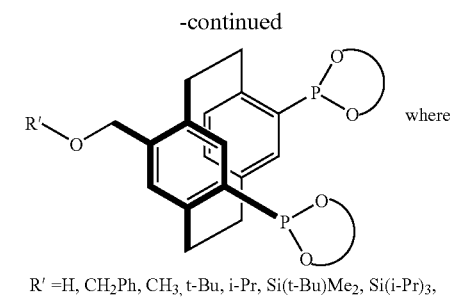

R' =H, CH₂Ph, CH₃, t-Bu, i-Pr, Si(t-Bu)Me₂, Si(i-Pr)₃,

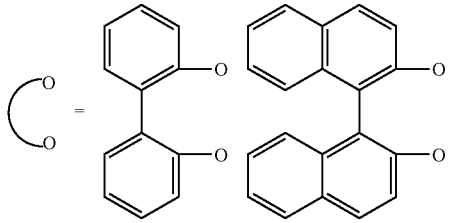

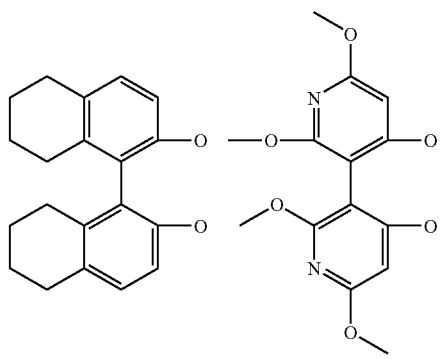

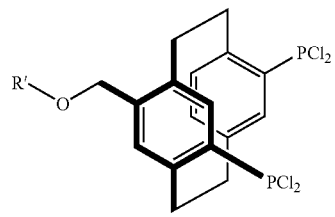

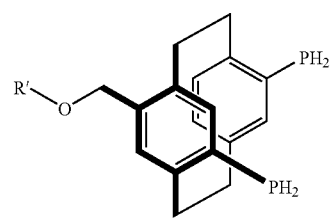

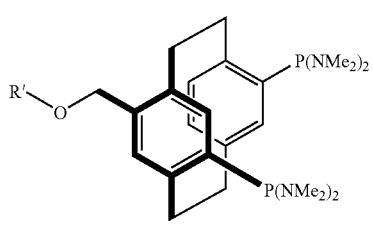

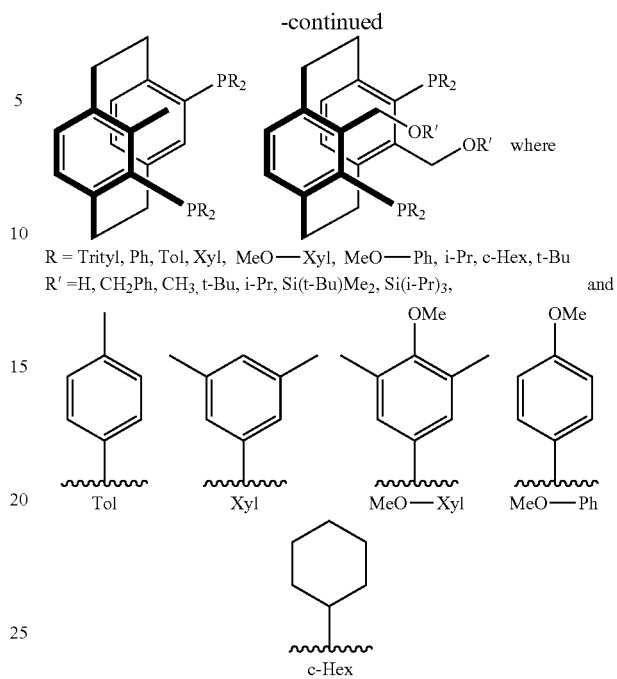

R = Trityl, Ph, Tol, Xyl, MeO—Xyl, MeO—Ph, i-Pr, c-Hex, t-Bu
R' =H, CH₂Ph, CH₃, t-Bu, i-Pr, Si(t-Bu)Me₂, Si(i-Pr)₃, and Methods for preparing the paracyclophane of the present invention include electrophilic substitution (including Friedel Crafts alkylation and acylation reactions), nucleophilic substitution, and metallation-substitution reactions on a suitable paracyclophane intermediate. Alternatively the substituted paracyclophane may be constructed by coupling or dimerisation of suitably substituted and functional benzene ring units by e.g. thermal or photochemical means. Preferably the substituted paracyclophane of the present invention is prepared by substitution reactions on a suitable paracyclophane intermediate. In particular, we have found that substituted pseudo-ortho dibromo-paracyclophane provides a very useful starting point for the synthesis of the substituted paracyclophane of the present invention.

Accordingly, the present invention further provides a method for preparation of a substituted paracyclophane of formula (I) by,

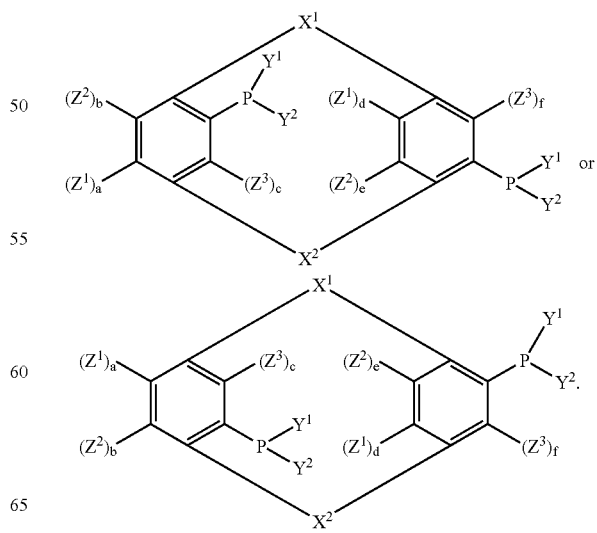

(a) performing a substitution reaction on a pseudo-ortho dibromoparacyclophane to form an intermediate substituted pseudo-ortho dibromoparacyclophane of formula (II), and

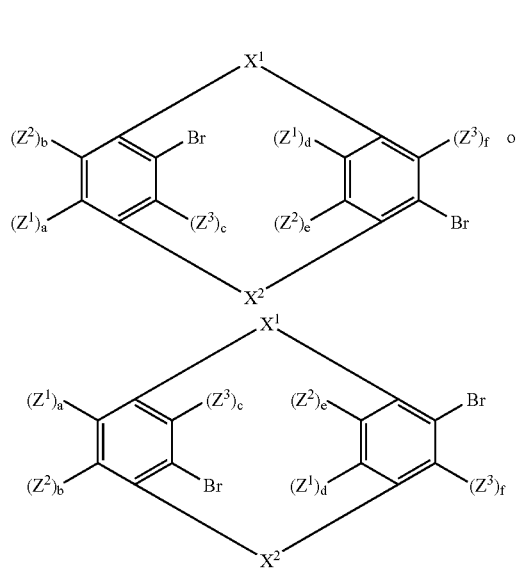

(II)

(b) reacting the substituted pseudo-ortho dibromoparacyclophane with a phosphorus compound comprising $P(Y^1Y^2)$, wherein $X^1$ and $X^2$ are linking groups comprising between 2 to 4 carbon atoms, $Y^1$ and $Y^2$ are selected from the group consisting of hydrogen, halide, oxygen, nitrogen, alkyl, cycloalkyl, aryl or heteroaryl, $Z^1$, $Z^2$ and $Z^3$ are substituting groups that optionally contain functional groups, wherein a, b, c, d, e and f are 0 or 1 and a+b+c+d+e+f=1 to 6.

The pseudo-ortho dibromoparacyclophane from which the substituted dibromoparacyclophane (II) is synthesised may be prepared according to known methods. Typically a paracyclophane may be reacted with bromine in the presence of iron in a suitable solvent (see D. J. Cram et al, *J. Am. Chem. Soc.*, 1969, 91, (13), 3527). In particular, for commercially available [2.2]paracyclophane, the synthesis of the pseudo-ortho dibromo[2.2]paracyclophane may be performed according to the methods described in example 1 and example 2 on pages 31 and 32 of aforesaid WO 97/47632.

Electrophilic substitution reactions are preferred for preparing the substituted paracyclophane of the present invention. In particular, we have found that the Lewis-acid mediated electrophilic substitution of a pseudo-ortho dibromoparacyclophane, particularly the pseudo-ortho dibromo [2.2]paracyclophane, proceeds surprisingly to substantially only the mono-para-substituted reaction product in high yield and selectivity. By forming only a mono-substituted product, the method is highly efficient and overcomes the possibility of having to perform complex and expensive separation techniques to obtain the desired substituted paracyclophane product.

For example, acetylation of pseudo-ortho dibromo[2,2] paracyclophane proceeds smoothly in the presence of aluminium trichloride ($AlCl_3$) and acetyl chloride ($CH_3COCl$) in dichloromethane (DCM) and surprisingly affords the mono-substituted acetylated product, with the ketone group exclusively in the para position. Even in the presence of excess Lewis acid no di-acetylated product was obtained. This reaction is depicted below;

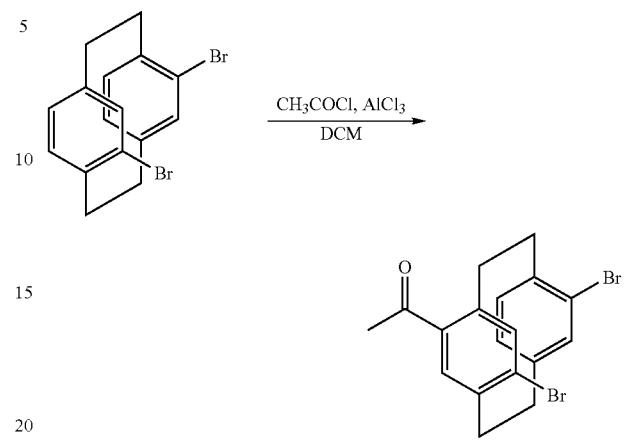

Scheme 1

In the presence of oxalyl chloride and $AlCl_3$ the pseudo-ortho dibromo[2,2]paracyclophane mono-acid chloride can be produced in high yield. This can either be hydrolysed in the presence of water or quenched with the methanol to give the methyl ester. These reactions are depicted below;

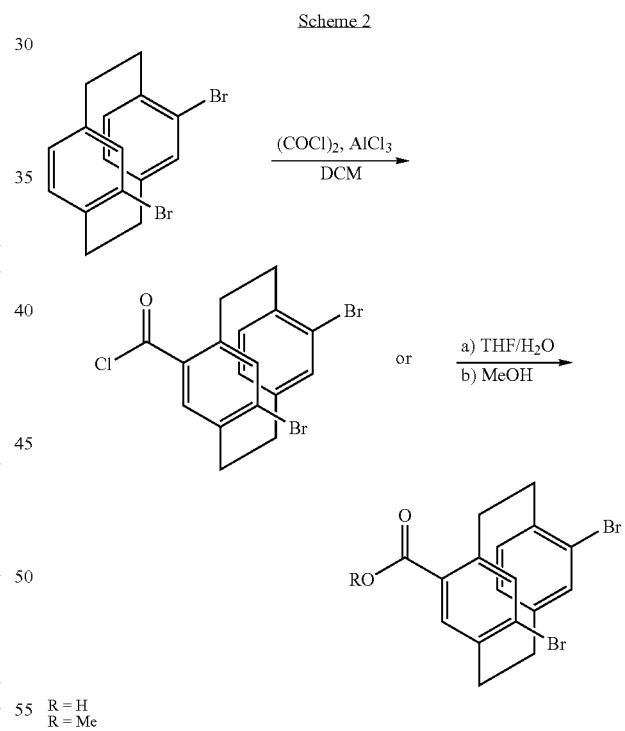

Scheme 2

R = H
R = Me

Under standard nitration conditions (conc $HNO_3$/acetic anhydride) both mono- and di-substituted pseudo-ortho dibromo[2,2]paracyclophane compounds could be obtained as well as some decomposition of the starting material. However, under preferred Lewis Acid nitration conditions ($Sc(OTf)_3$) a higher yield of the pseudo-ortho dibromo[2,2] paracyclophane mono-nitro compound was obtained with no di-substituted product detected. These reactions are depicted below;

Scheme 3

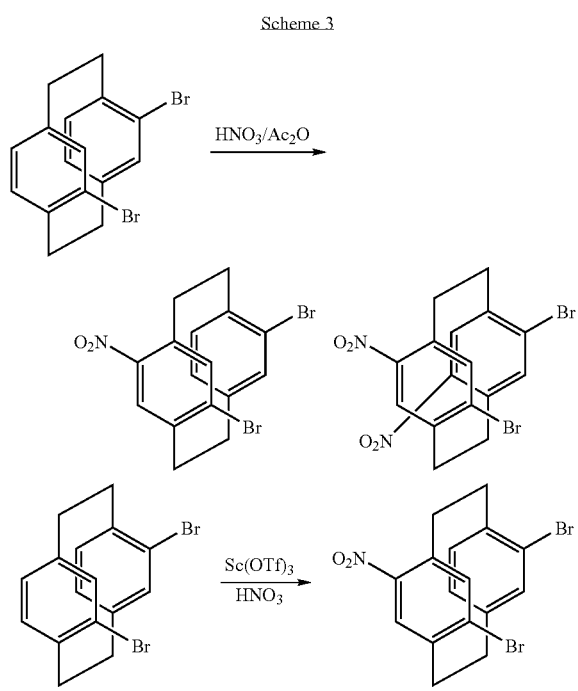

Ortho-substitution may be accomplished using a method of ortho-lithiation wherein a paracyclophane substituted with an ortho-directing group, e.g. 4-N,N-diethylamido-[2.2]paracyclophane is lithiated using a suitable alkyllithium compound, e.g. t-butyl lithium in diethyl ether and TMEDA, and the resulting lithiated paracyclophane treated with a suitable electrophile (see Pelter et al, *Tetrahedron Lett.*, 2001, 8391-4).

The functional groups on the substituted pseudo-ortho dibromoparacyclophane(II) may, if desired, be chemically transformed before it is converted into the desired phosphine, phosphonite, phosphorus-amide or phosphonamidite-containing paracyclophane of formula (I). For example, where the substituting group is a nitro (—NO$_2$) group it may be reduced using known techniques such as catalytic hydrogenation to an amino (—NH$_2$) group. Alternatively, a hydroxyl functionality may be provided by reduction of e.g. the methyl ester product depicted in Scheme 2 using LiAlH$_4$ to give the corresponding benzyl alcohol. However, prior to conversion of the benzyl alcohol-substituted pseudo-ortho dibromoparacyclophane into the corresponding phosphine, phosphonite or phosphonamidite, the hydroxyl group may be converted to another substituting group, e.g. a trityl group or tri-isopropoxysilyl group. The trityl-conversion reaction is depicted below.

Scheme 4

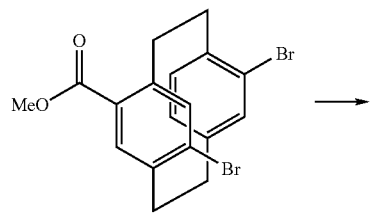

-continued

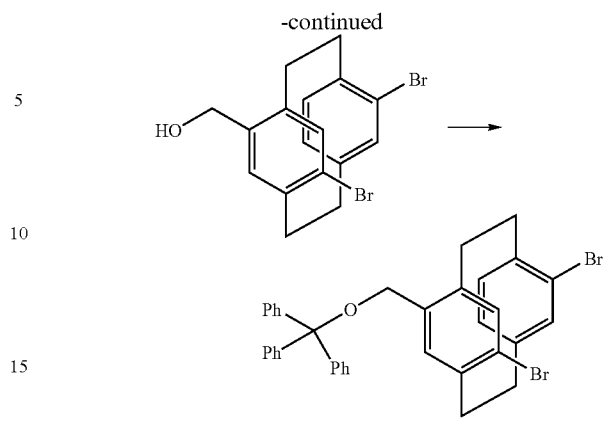

If desired the hydroxyl functional group may be regenerated from the trityl group by treatment of the resulting trityl-functionalised substituted paracyclophane with a suitable acid. Similarly, the tri-isopropylsilyl group may be removed using tetrabutylammonium fluoride (TBAF).

Once the substituted pseudo-ortho dibromoparacyclophane(II) has been synthesised, the next step of the method of the present invention is the conversion of the pseudo-ortho bromide groups to the desired phosphine, phosphonite, phosphorus amide or phosphonamidite by reacting the substituted pseudo-ortho dibromoparacyclophane(II) with a phosphorus compound comprising P(Y$^1$Y$^2$). This reaction may be performed according to a number of known methods. For example direct displacement of the Br atoms by diphenylphosphino groups may be achieved by reaction of the substituted pseudo-ortho dibromoparacyclophane(II) with diphenylphosphine (Ph$_2$PH) in the presence of NiCl$_2$.dppe and triethylenediamine in DMF at 100° C., or by using the lithiated diphenylphosphine (Ph$_2$PLi) with NiCl$_2$.dppe in THF at room temperature. Alternatively, a low temperature lithiation with BuLi and transmetallation using MgBr$_2$ leads to an active Grignard reagent that may be combined with the more stable phosphoryl oxide (Ph$_2$P(O)Cl). The Grignard may also be formed directly by reaction of Mg with the substituted pseudo-ortho dibromide (II). The resulting bis(phosphine oxide) paracyclophane is then reduced to the desired bis phosphine using a suitable reducing agent, e.g. HSiCl$_3$ or LiAlH$_4$.

Preferably, substituted paracyclophane bis(phosphines) are prepared by treating the substituted pseudo-ortho dibromoparacyclophane of formula (II) with an alkyl lithium reagent, e.g. tert-Butyl Lithium (tBuLi) and the anion quenched with an aryl- or alkyl-phosphinylchloride, e.g. diphenylphosphinylchloride (Ph$_2$PCl) to give the desired substituted paracyclophane bis(phosphine). A similar method may be used for other aryl and alkyl phosphines. Using the trityl-protected pseudo-ortho dibromo[2,2]paracyclophane of Scheme 4, this reaction may be depicted as follows;

Scheme 5

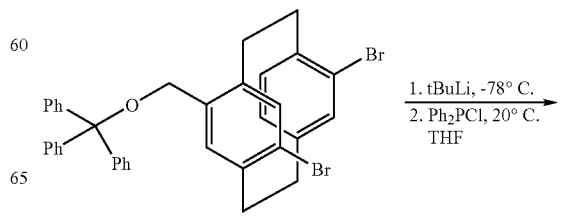

-continued

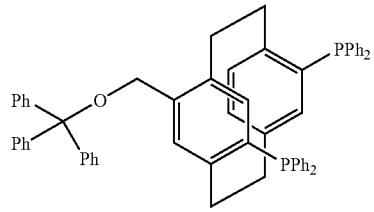

Alternatively, the more air and moisture-stable corresponding phosphine oxide may be prepared using Ph₂POCl and the phosphine oxide subsequently reduced using e.g. HSiCl₃.

Methods suitable for preparing a phosphonite, phosphorus amide and phosphonamidite from the substituted pseudo-ortho dibromoparacyclophane of formula (II) may be found in A. Zanotti-Gerosa et al, *Org. Lett.,* 2001, 3687.

A substituted pseudo-ortho dibromoparacyclophane may be converted to the corresponding substituted paracyclophane bis(phosphonite) in an analogous manner to the phosphine by direct metallation of the dibromide with a strong organometallic base and reaction with the appropriate chloro-phosphonite. Preferably, the substituted paracyclophane bis(phosphonite) may be synthesised by treatment of a substituted paracyclophane bis(dichlorophosphine) or substituted paracyclophane phosphorus-diamide with an alcohol, diol or metal diolate. The substituted paracyclophane bis(dichlorophosphine) may itself be obtained via the paracyclophane phosphorus diamide which may be prepared by direct metallation of the paracyclophane dibromide with a strong organometallic base and reaction with a chloro-phosphorus-diamide such as Cl—P(NCH₃)₂ or ClP(iso-C₃H₇). The resulting paracyclophane phosphorus-diamide may be converted to the paracyclophane bis(dichlorophosphine) by treatment with an HCl solution. These reactions are depicted for a substituted [2.2]paracyclophane below;

To prevent unwanted side reactions during the described sequence of reactions, the substituting group may where appropriate be protected, e.g. by an alkoxy group using known methods.

The substituted paracyclophane of the present invention is chiral and may adopt one of two enantiomeric forms i.e. an (R)- or (S)-configuration. Accordingly, the paracyclophane may comprise a racemic mixture of enantiomers. Alternatively and preferably the substituted paracyclophane comprises a substantially enantiomerically-pure enantiomer (i.e having an enantiomeric excess >75%, preferably >95%). To obtain a substantially pure enantiomer the substituted paracyclophane may be prepared from a substantially enantiomerically-pure pseudo-ortho dibromoparacyclophane starting material. For example, resolution of a racemic mixture of pseudo-ortho dibromoparacyclophane may be effected on a chiral stationary phase such as crystalline cellulose triacetate using ethanol as eluant or on chiral HPLC columns. Alternatively, a chiral resolution may be performed at later stages during the synthetic process. For example, the resolution may be performed on the substituted paracyclophane bis(phosphine), phosphine oxide, phosphonite, phosphorus amide or phosphonamidite(I) using known crystallisation techniques or separation on chiral chromatography columns. For example, resolution may be effected by treatment of a substituted paracyclophane phosphine oxide to form inclusion complexes with chiral substances such as benzoyl tartaric acid: the resolved phosphine oxide then is reduced using e.g. HSiCl₃. These methods however have a disadvantage in that they can be expensive and time-consuming.

Advantageously, in the present invention, the chiral resolution of the paracyclophane may, if desired, be achieved utilising the substituting group itself. This resolution is preferably performed using a substituted pseudo-ortho dibromoparacyclophane having a suitable functional group on a substituting group.

Scheme 6

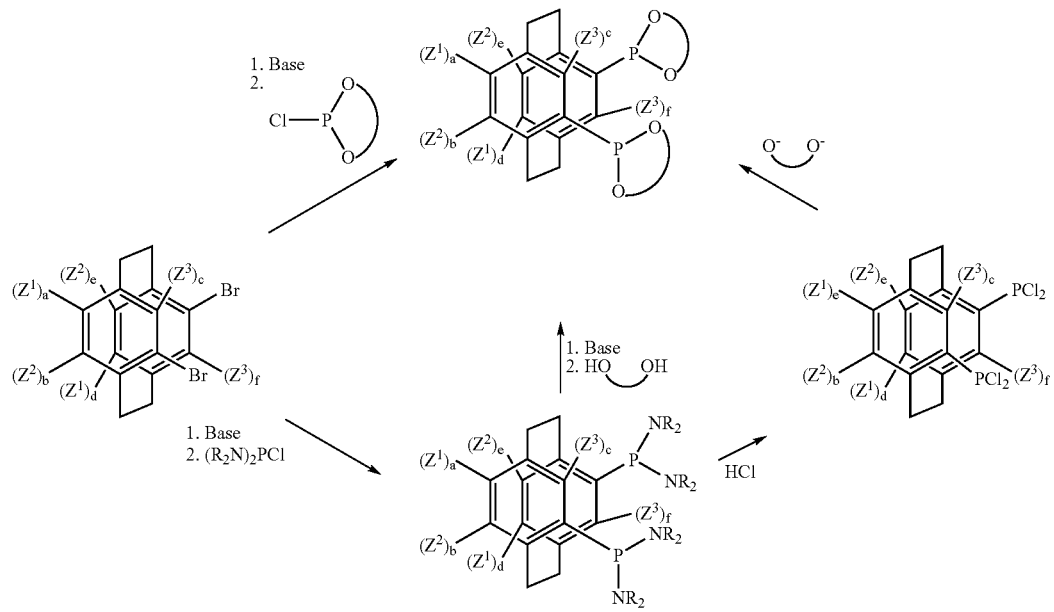

Accordingly, the invention further provides a substituted pseudo-ortho dibromoparacyclophane of formula (III)

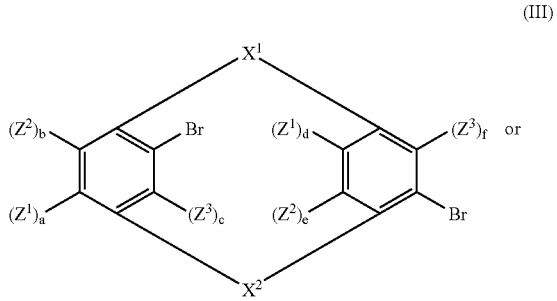

(III)

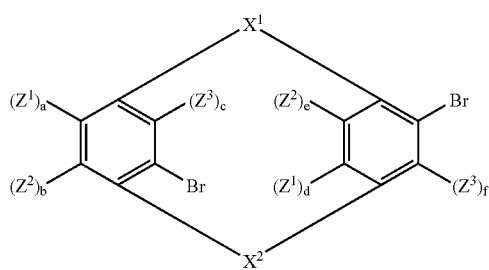

wherein $X^1$ and $X^2$ are linking groups comprising between 2 to 4 carbon atoms, $Z^1$, $Z^2$ and $Z^3$ are substituting groups at least one of which comprises a functional group selected from hydroxyl, alkoxy, carboxyl, anhydride, methacryl, epoxide, vinyl, nitrile, nitro, sulphate, sulphonyl, mercapto, sulphide amino, amine, imine, and imide, a, b, c, d, e and f are 0 or 1 and a+b+c+d+e+f=1 to 6.

Preferably the functional group is a carboxylic acid (—COOH) functional group that may be reacted with a chiral base, or an amino functional group (—NH₂, formed for example, by reduction of a nitro, —NO₂, group) that may be reacted with a chiral acid. Alternatively, the functional group may be one that may interact with an enzyme to allow enzymitic chiral resolution. Preferably one or two, more preferably one functional group-containing substituting group is present in the substituted pseudo-ortho dibromoparacyclophane of formula (III), i.e. preferably a+b+c+d+e+f=1 or 2, more preferably a+b+c+d+e+f=1 and most preferably a or d=1.

The use of the substituted pseudo-ortho dibromoparacyclophane of formula (III) provides a number of advantages, in particular the simplification of the synthetic process to the desired chiral product. In one embodiment, the mono-substituted paracyclophane carboxylate of Scheme 2 may be used to effect chiral resolution of the pseudo-ortho dibromide before synthesis of the paracyclophane phosphine, phosphonite, phosphorus-amide or phosphonamidite. The sequence of steps leading to chiral resolution of a mono-para-substituted pseudo-ortho dibromo[2.2]paracyclophane using a chiral base is depicted below;

Scheme 7

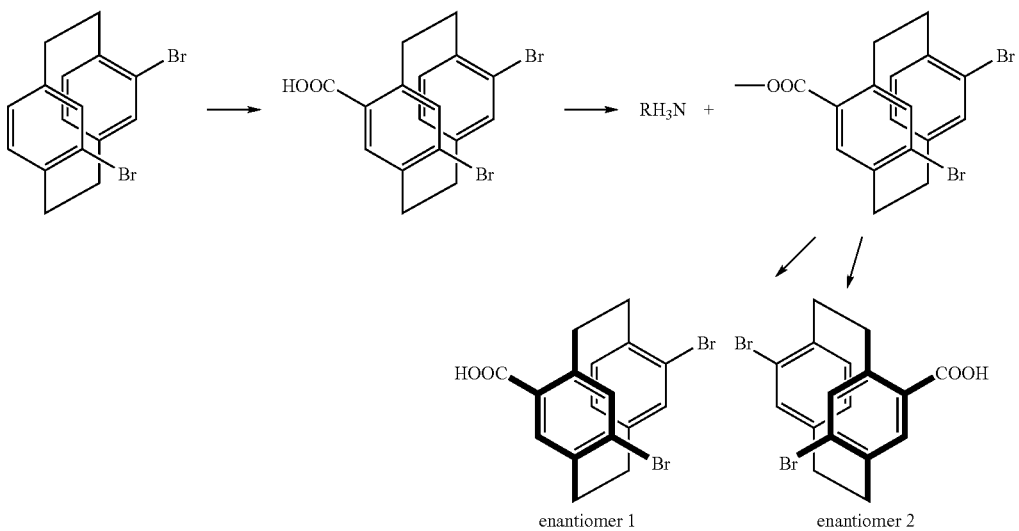

enantiomer 1   enantiomer 2

The chiral resolution may be effected using known techniques using a chiral base such as cinchonidine. Alternatively, the resolution may be performed on an amino-substituted pseudo-ortho dibromoparacyclophane using a chiral acid e.g. tartaric acid and tartaric acid esters, mandelic acid or camphor sulphonic acid.

It will be understood by those skilled in the art that where one enantiomer of a substituted paracyclophane is depicted, the other is included within the scope of the present invention. The substituted paracyclophane(I) of the present invention may be used as a ligand to prepare metal complexes suitable for use as catalysts in chemical reactions.

Accordingly the invention further provides a metal complex comprising the reaction product of a metal compound and a substituted paracyclophane of formula (I)

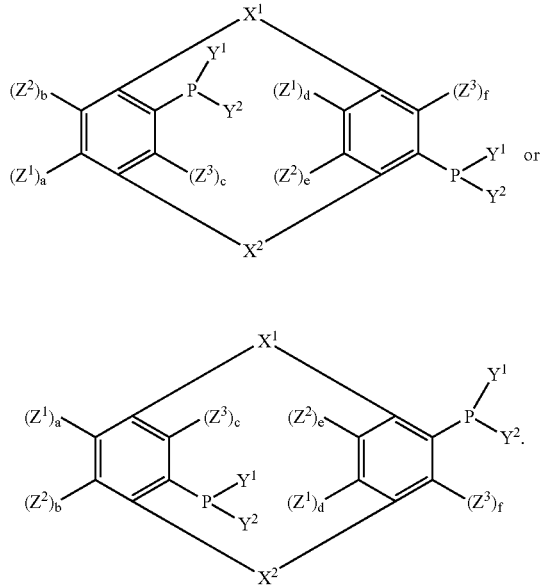

wherein $X^1$ and $X^2$ are linking groups comprising between 2 to 4 carbon atoms, $Y^1$ and $Y^2$ are selected from the group consisting of hydrogen, halide, oxygen, nitrogen, alkyl, cycloalkyl, aryl or heteroaryl, $Z^1$, $Z^2$ and $Z^3$ are substituting groups that optionally contain functional groups, a, b, c, d, e and f are 0 or 1 and a+b+c+d+e+f=1 to 6.

The substituted paracyclophane(I) may be combined with the metal compound in a racemic mixture or in a substantially enantiomerically pure form. Preferably the substituted paracyclophane(I) is substantially enantiomerically-pure (i.e having an enantiomeric excess >75%, preferably >95%). The metal compound may be any metal compound that is able to react with the substituted paracyclophane(I) to provide a metal complex. The metal compound is preferably a compound of palladium (Pd), platinum (Pt), rhodium (Rh), iridium (Ir) or ruthenium (Ru) which may be a metal salt, e.g. halide, carboxylate, sulphonate or phosphonate, or an organometallic compound. The metal complex may additionally comprise ligands that are able to reversibly co-ordinate. Reversibly co-ordinating ligands may improve the stability of the metal complexes and may be provided during the synthesis of the metal complex or may react with the metal complex when it is added to the reaction mixture. By "reversibly co-ordinating" we mean a ligand that can be readily displaced by other molecules in a reaction mixture. Such reversibly co-ordinating ligands may be selected from the list comprising dienes, particularly cyclic dienes such as cyclooctadiene or norbornadiene, C1-C4 alcohols, ethers, cyclic ethers, diols, e.g. 1,2-diols and C2 or C3 olefins, e.g. ethylene. In addition, the metal complex may additionally comprise a non-reversibly co-ordinating ligand that may be used to modify the reactivity and selectivity of the metal complex catalyst. Non-reversibly co-ordinating ligands that may be used particularly in Rh complexes are diamines, for example 1,2-diphenylethylenediamine, 1,2-cyclohexylethylenediamine and ethylene diamine and particularly substantially enantiomerically-pure chiral 1,2-diamines such as (S,S)-1,2-diphenylethylenediamine.

To satisfy the oxidation state of the metal complex, it may when the oxidation state of the metal requires, further comprise a counter-ion. The counter-ion may be any suitable anion but is preferably a non-nucleophile anion selected from trifluoromethanesulphonate (triflate or OTf), perchlorate ($ClO_4$), hexafluoroantimonate ($SbF_6$) or hexafluorophosphate (PF6).

Accordingly, metal complexes of the present invention include but are not limited to the following;

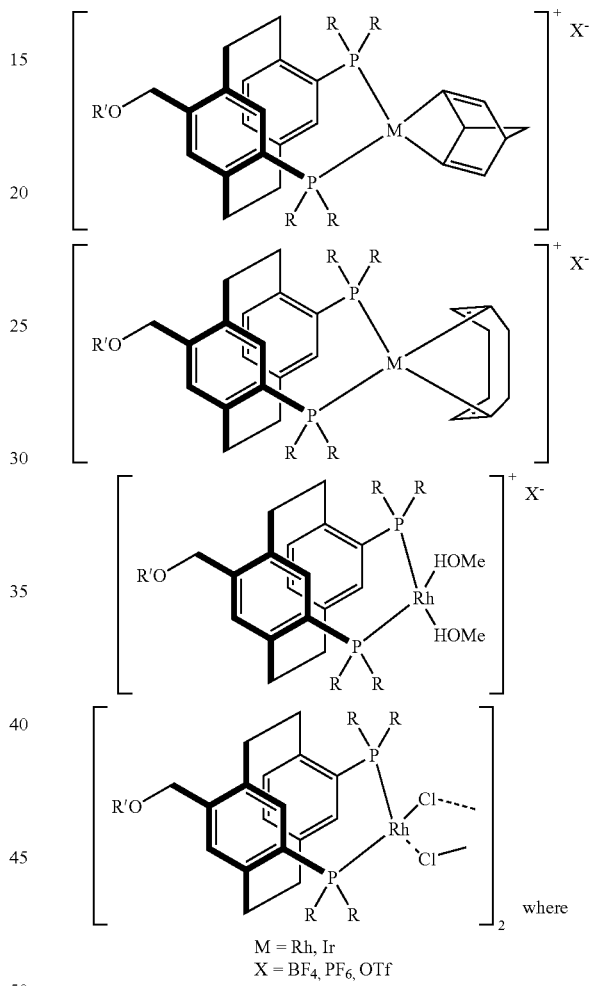

M = Rh, Ir
X = $BF_4$, $PF_6$, OTf

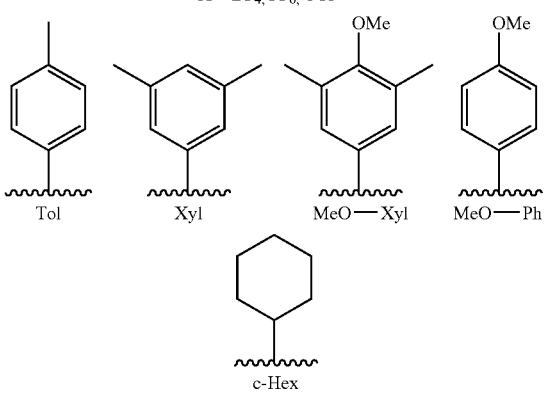

R = Ph, Tol, Xyl, MeO—Xyl, MeO—Ph, i-Pr, c-Hex, t-Bu
R' = H, $CH_2Ph$, $CH_3$, t-Bu, i-Pr, Si(t-Bu)$Me_2$, Si(i-Pr)$_3$,

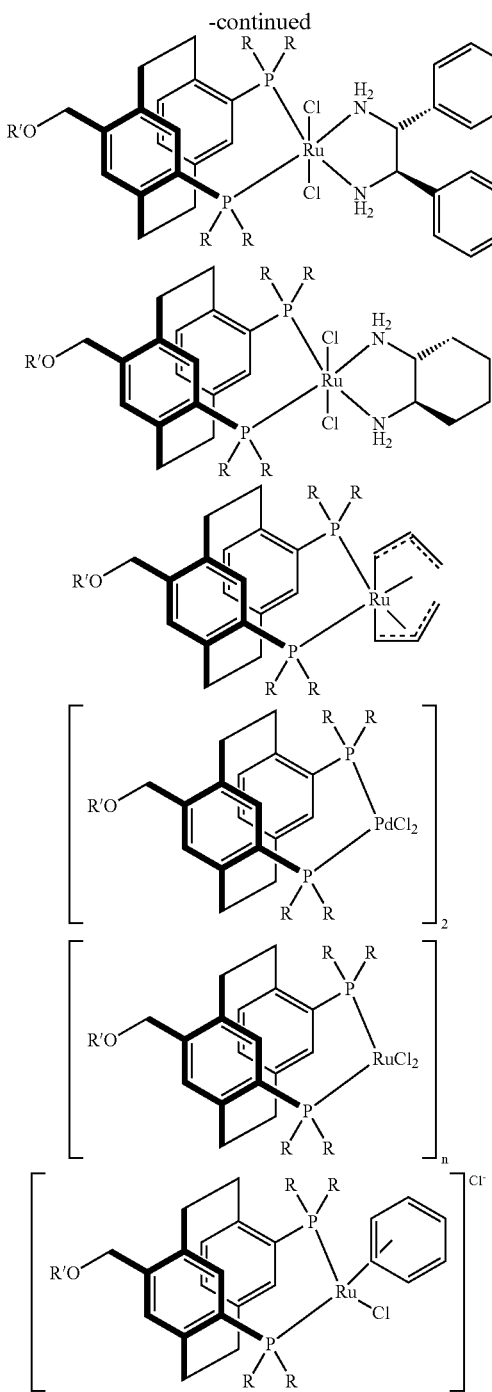

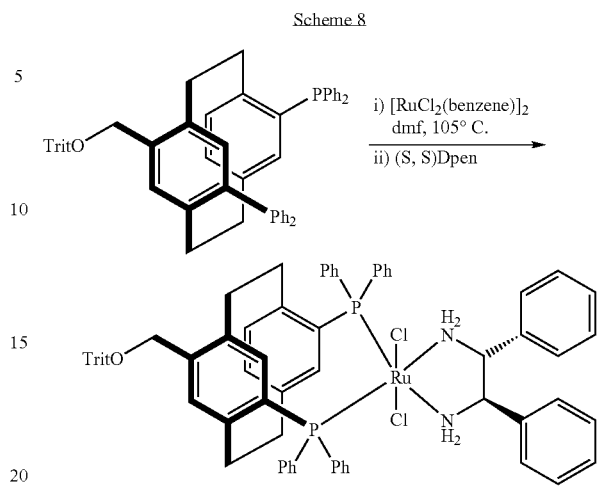

Scheme 8

The substituted paracyclophane ligands of the present invention are chiral and therefore are able to produce chiral metal complex catalysts. The chiral metal complex catalysts of the present invention may be applied to a large number of asymmetric reactions used to produce chiral products. Such reactions include but are not limited to asymmetric hydrogenation reactions such as the chiral hydrogenation of enamide and non-enamide structures, asymmetric hydrogenation in iso-quinoline synthesis, the asymmetric hydrogenation of unsaturated alcohols, and the asymmetric hydrogenation of ketones and imines. The catalysts of the present invention may also be used for carbon-carbon coupling reactions such as the Heck or Suzuki reactions, for the enantioselective isomerization of olefins, asymmetric hydroboration reactions, asymmetric cyclisation of olefinic aldehydes, asymmetric arylation and alkylation reactions and the amination of aryl halides (Hartwig-Buchwald reaction). Where appropriate, to achieve high levels of enantiomeric purity in a reaction it is preferred that the metal complex comprises a substantially enantiomerically-pure substituted paracyclophane(I).

The conditions for using the metal complex catalysts are typically similar to those used for structurally related catalysts. For example, for the asymmetric reduction of ketones, the catalyst prepared according to scheme 7 may be used at room temperature under standard hydrogen pressures. The reaction may be depicted as follows;

The metal complexes may be readily prepared from the substituted paracyclophane of the present invention. In general, the metal compound is combined with the substituted paracyclophane and optionally the reversibly coordinating ligand and/or non-reversibly co-ordinating ligand in a suitable solvent and heated if necessary to form the desired metal complex. For example, the alkoxy-substituted paracyclophane bis(phosphine) of Scheme 5 reacts under relatively mild conditions with [RuCl$_2$(benzene)$_2$]$_2$ and (S,S)-Dpen to form a catalyst suitable for performing asymmetric reduction reactions. This reaction is depicted below.

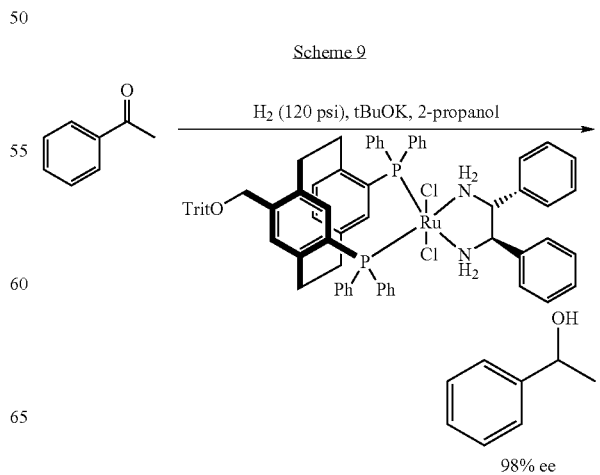

Scheme 9

98% ee

While we have found the metal complexes comprising substituted paracyclophanes of the present invention to be highly effective homogeneous catalysts it is desirable to provide such metal complexes on solid supports as heterogeneous catalysts. Heterogeneous catalysts have the advantages that they are often easier to separate from the reaction mixtures and may in some circumstances be recycled. To form a heterogeneous catalyst, the metal complex may be absorbed or ion-exchanged into a suitable solid support material, e.g. a zeolite. Alternatively the metal complex may be reacted with functional groups present on a solid support material to form a covalently bound catalyst. Covalently-bound heterogeneous catalysts are often preferred as they can be more resistant to leaching of the metal complex in use than the absorbed or ion-exchanged heterogeneous catalysts. Advantageously, the substituted paracyclophanes of the present invention possess substituting groups that may contain functional groups that are capable of reacting with functional groups present on the solid support material.

A number of routes are possible for forming a covalently-bound heterogeneous catalyst using the paracyclophanes of the present invention.

(i) the metal complex derived from substituted paracyclophane(I) having functional group-containing substituting groups may simply be reacted with functional groups present on the insoluble solid support material.

(ii) The substituted paracyclophane(I) having functional group-containing substituting groups may be reacted with functional groups present on an insoluble solid support material and the metal compound subsequently reacted with it to prepare a supported metal complex.

(iii) The substituted dibromoparacyclophane(II) having functional group-containing substituting groups may be reacted with the functional groups present on a solid support material and then converted to the substituted paracyclophane(I) before subsequently reacting the supported paracyclophane with the metal compound to form the supported metal complex.

Furthermore, if a functional group present in substituting groups $Z^1$, $Z^2$ or $Z^3$ is unsuitable for reaction with a given solid support material, it may be inter-converted by chemical reaction (e.g. reduction or oxidation) or alternatively, the functional group may be reacted with a linker molecule that provides a suitable functional group capable of reaction with said solid support.

The solid support materials to which the substituted paracyclophane may be covalently bonded, may be polymers, metal oxides or sol-gel materials that have sites capable of reacting with functional groups present in substituting groups $Z^1$, $Z^2$ or $Z^3$. The reactive sites present in the solid support materials may be selected from halide (Cl, Br, F, or I), hydroxyl, carbonyl, carboxyl, anhydride, methacryl, epoxide, vinyl, nitrile, mercapto, isocyanate, amine, imine, amide and imide, and are typically provided by surface functionalisation of the solid supports using known methods, e.g. grafting using organofunctional silanes. The metal oxides include silica, titania, zirconia or alumina, aluminosilicates or mixtures of these. The polymer may be any thermoplastic polymer that is insoluble in the solvent system used for performing the catalysed reaction and is stable under the reaction conditions. Preferably, where the reaction is performed in polar solvents, the polymer is a polyolefin copolymer, for example an acrylate/polyacrylic acid polyolefin copolymer of suitable molecular weight. Such polymers contain carboxyl (COOH) groups able to react with e.g. a hydroxyl (OH) or an amine ($NH_2$) group present in substituting groups $Z^1$, $Z^2$ or $Z^3$. Advantageously, the polymers may be formed into fibres or pellets that may readily be removed from the reaction mixture. By the term "sol-gel materials" we mean organofunctional silica materials prepared, for example, by hydrolysis of organofunctional silanes, preferably in the presence of alkyl silicates and optionally other metal alkoxides, for example according to the methods described in WO 02/066159.

The solid support material may be in the form of powder, pellets, granules, fibres, a honeycomb or foam.

The invention is further illustrated by reference to the following examples where MTBE=methyl-t-butyl ether; DMF=dimethylformamide; DMAP=2,6-dimethylaminopyridine Dpen=1,2-Diphenylethylenediamine; NBD=norbornadiene, DBU=1,8-diazabicyclo-[5.4.0]-undec-7-ene and room temperature=20-25° C. unless otherwise stated. The nomenclature of the substituted paracyclophanes was assigned as in: S. Gisbon et al. *Organic and Biomolecular Chemistry* 2003, 1256.

EXAMPLE 1

Synthesis of nitro[2.2]paracyclophane derivatives a) Standard Nitration: Preparation of 4,12-dibromo-7-nitro[2.2]paracyclophane and 4,12-dibromo-7,15-dinitro[2.2]paracyclophane.

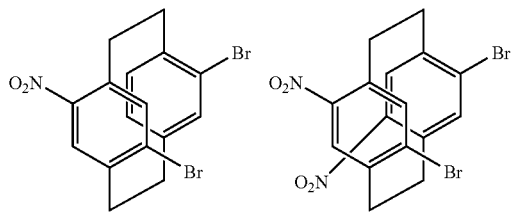

A solution of $HNO_3$ conc. (0.6 mL) in acetic anhydride (1.4 mL) was added to a suspension of 4,12-dibromo[2.2]paracyclophane (1.098 g, 3 mmol) in acetic anhydride (2 mL) cooled to 0° C. The reaction was stirred at room temperature for 1.5 hours. The resulting yellow solution was diluted with water (100 mL) and extracted with ethyl acetate (2×50 mL). The combined organic layers were washed with more water, dried over anhydrous $Na_2SO_4$ and evaporated to give a yellow oil that was purified by chromatography (eluant: hexane/ethyl acetate 19/1) to give 4,12-dibromo-7-nitro-paracyclophane (105 mg, 8.5% yield) and 4,12-dibromo-7,15-dinitro-paracyclophane (110 mg, 8% yield).

b) Lewis acid mediated nitration: preparation of 4,12-dibromo-7-nitro[2.2]paracyclophane $Sc(OTf)_3$ (100 mg, 0.2 mmol) was suspended in dichloroethane (2.5 mL) and $HNO_3$ 70% (0.1 mL) was added to give a clear solution at room temperature. 4,12-Dibromo-[2.2]paracyclophane (366 mg, 1 mmol) was added and the reaction was heated to 70° C. and stirred for 20 hours. After this time, thin-layer chromatographic (TLC) analysis (eluant:hexane/MTBE 95/5) indicated that the reaction was not complete and more $Sc(OTf)_3$ (100 mg, 0.2 mmol) and $HNO_3$ 70% (0.1 mL) were added. After 1 hour at 70° C. all the starting material was consumed and the reaction was diluted with dichloromethane (50 mL) and washed with brine (2×50 mL). The organic phase was dried over anhydrous $Na_2SO_4$ and evaporated to give a yellow oil. The crude material was dissolved in 2 mL dichloromethane and eluted through a pad of silica gel (eluant hexane/MTBE 9/1). Evaporation of the solvent gave 4,12-dibromo-7-nitro[2.2]paracyclophane (190 mg, 31% yield) as a yellow solid.

4,12-dibromo-7-nitro[2.2]paracyclophane: $^1$H NMR (CDCl$_3$, 400 MHz): 2.75 (1H, m, —CH$_2$—), 3.0 (4H, m, —CH$_2$—), 3.4 (2H, m, —CH$_2$—), 3.3 (1H, m, —CH$_2$—), 6.4 (1H, d, CH arom), 6.6 (1H, d, CH arom), 7.1 (1H, s, CH arom), 7.25 (1H, s, CH arom), 7.3 (1H, s, CH arom) ppm. $^{13}$C NMR (CDCl$_3$, 400 MHz): 32.1 (—CH$_2$—), 32.6 (—CH$_2$—), 35.1 (—CH$_2$—), 35.2 (—CH$_2$—), 127.0 (C arom), 130.9 (CH arom), 131.2 (CH arom), 132.0 (CH arom), 132.6 (C arom), 133.3 (CH arom), 136.2 (CH arom), 137.7 (C arom), 138.9 (C arom), 140.9 (C arom), 141.4 (C arom), 148.6 (C—NO$_2$ arom) ppm. 4,12-dibromo-7,15-dinitro[2.2]paracyclophane: $^1$H NMR (CDCl$_3$, 400 MHz): 3.1 (4H, m, —CH$_2$—), 3.4 (2H, m, —CH$_2$—), 3.8 (2H, m, —CH$_2$—), 7.3 (4H, s, broad, CH arom) ppm. $^{13}$C NMR (CDCl$_3$, 400 MHz): 30.9 (—CH$_2$—), 33.4 (—CH$_2$—), 126.9 (CH arom), 131.6 (C arom), 135.5 (CH arom), 135.7 (C arom), 140.4 (C arom), 147.4 (C—NO$_2$ arom) ppm.

EXAMPLE 2

Synthesis of acetyl[2.2]paracyclophane derivatives a) Preparation of 7-acetyl-4,12-dibromo[2.2]paracyclophane

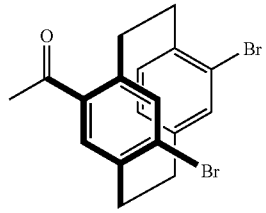

A solution of AlCl$_3$ (266 mg, 2 mmol) and acetyl chloride (0.145 mL, 2 mmol) in anhydrous dichloromethane CH$_2$Cl$_2$ (2.5 ml) was added to a solution of (R)-4,12-dibromoparacyclophane (366 mg, 1 mmol) in CH$_2$Cl$_2$ (10 ml) at −45° C. The mixture was allowed to warm to room temperature. After 30 mins the reaction mixture was poured into a flask containing dilute 2M aq. HCl (50 ml) and ice. Methyl-t-butyl ether MTBE (50 ml) was added and the organic layer further washed with saturated solution of NaHCO$_3$ (50 ml), brine (50 ml) and dried further with anhydrous MgSO$_4$, filtered and the solvent removed to give the crude product which was substantially pure by NMR.

EXAMPLE 3

Synthesis and resolution of carboxylic acid[2.2]paracyclophane derivatives a) Preparation of 7-chlorocarbonyl-4,12-dibromo[2.2]paracyclophane

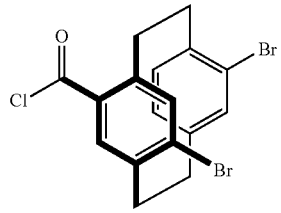

Oxalyl chloride (0.35 mL, 4 mmol) was added dropwise to a suspension of AlCl$_3$ (260 mg, 2 mmol) in CH$_2$Cl$_2$ (2 mL). After stirring for 30 min at room temperature, the obtained solution was cooled down to 0° C. and treated with a solution of (R)-4,12-dibromo[2.2]paracyclophane (366 mg, 1 mmol) in CH$_2$Cl$_2$ (2 mL). The dark solution was then stirred at 0° C. for 30 min and allowed to warm up to room temperature for another 30 min. Solvents and volatile reagents were removed under vacuum to afford the product as a yellow solid.

b) Preparation of 4,12-dibromo-7-methoxycarbonyl[2.2]paracyclophane

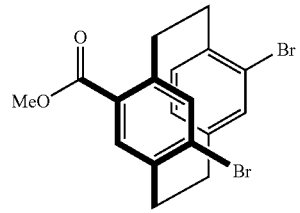

A solution of 7-chloroformyl-4,12-dibromo[2.2]paracyclophane (1 mmol) in CH$_2$Cl$_2$ (2 mL) was treated with methanol MeOH (3 mL) and stirred at 50° C. for 1 hour. After cooling down to room temperature and diluting with MTBE (10 mL), the organic phase was washed with 2.8 M NH$_4$Cl, H$_2$O and saturated aqueous NaHCO$_3$, dried over anhydrous MgSO$_4$ and concentrated under vacuum to afford the product (360 mg, 85% yield) as a pale yellow solid (mp=118.7° C.). $^1$H NMR (CDCl$_3$): 2.7-2.8 (m, 1H), 2.8-3.0 (m, 4H), 3.2-3.4 (m, 2H), 3.85 (s, 3H, CO$_2$CH$_3$), 3.7-3.9 (m, 1H), 6.38 (d, 1H, J=7.8 Hz), 6.43 (d, 1H, J=7.8 Hz), 7.10 (s, 1H), 7.11 (s, 1H), 7.17 (s, 1H) ppm. $^{13}$C NMR (CDCl$_3$): 32.2 (t), 32.7 (t), 35.4 (t), 35.5 (t), 52.0 (q), 126.6 (s), 130.3 (s), 131.1 (s), 131.2 (d), 132.8 (d), 133.3 (d), 135.1 (d), 136.8 (d), 139.1 (s), 139.2 (s), 141.0 (s), 144.0 (s), 166.8 (s, CO) ppm.

c) Preparation of 4,12-dibromo-7-tertbutoxycarbonyl[2.2]paracyclophane

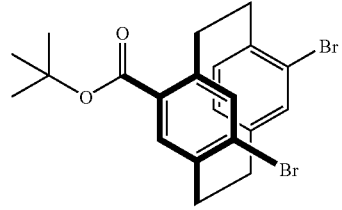

A solution of 7-chloroformyl-4,12-dibromo[2.2]paracyclophane (6 mmol) in CH$_2$Cl$_2$ (12 mL) was treated with tBuOH (12 mL) and stirred overnight at 50° C. After cooling down to room temperature and diluting with MTBE (25 mL), the organic phase was washed with 2.8 M NH$_4$Cl, H$_2$O and saturated aqueous NaHCO$_3$, dried over MgSO$_4$ and concentrated under vacuum to afford the product (2.2 g, 79% yield) as a white solid (mp=128.5° C.). $^1$H NMR (CDCl$_3$): 1.56 (s, 9H, tBu), 2.7-2.8 (m, 1H), 2.8-3.0 (m, 4H), 3.2-3.4 (m, 2H), 3.7-3.8 (m, 1H), 6.38 (dd, 1H, J=7.8, 1.8 Hz), 6.47 (d, 1 H, J=7.8 Hz), 7.05 (s, 1H), 7.08 (d, 1H, J=1.8 Hz), 7.13 (s, 1H) ppm. $^{13}$C NMR (CDCl$_3$): 27.7 (q, 3x, tBu), 31.6 (t), 32.3 (t), 34.8 (t), 35.1 (t), 80.7 (s), 80.7 (s), 126.0 (s), 129.9

(s), 130.6 (d), 131.7 (s), 132.2 (d), 132.7 (d), 134.5 (d), 136.5 (d), 138.4 (s), 138.5 (s), 141.5 (s), 142.8 (s), 165.2 (s, CO) ppm.

d) Preparation of 7-carboxy-4,12-dibromo[2.2]paracyclophane from acyl chloride

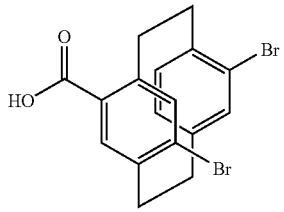

A solution of 7-chloroformyl-4,12-dibromo[2.2]paracyclophane (1 mmol) in THF (2 mL) was treated with $H_2O$ (1 mL) and stirred overnight at room temperature. The reaction mixture was then diluted with MTBE and washed with brine and $H_2O$. The organic phase was then dried (an $MgSO_4$) and concentrated under vacuum, the obtained solid was recrystallised from hot MTBE/hexane to afford the product (328 mg, 80% yield) as a white solid (mp=239.7° C.). $^1$H NMR ($CDCl_3$): 2.7-2.8 (m, 1H), 2.9-3.0 (m, 4H), 3.2-3.4 (m, 2H), 3.8-3.9 (m, 1H), 6.42 (d, 1H, J=7.8 Hz), 6.52 (d, 1H, J=7.8Hz), 7.10 (s, 1H), 7.17 (s, 1H), 7.18 (s, 1H) ppm. $^{13}$C NMR ($CDCl_3$): 31.6(t), 32.2 (t), 32.8 (t), 35.4(t), 126.7 (s), 129.2 (s), 131.2 (d), 132.3 (s), 132.8 (d), 133.4 (d), 135.4 (d), 137.6 (d), 139.2 (s), 139.5 (s), 141.1 (s), 145.1 (s), 171.6 (s, CO) ppm. (S)-7-carboxy-4,12-dibromo[2.2]paracyclophane: $[\alpha]_D$=+217.5 ($CH_2Cl_2$, c=16.4 mg/mL).

e) Preparation of 7-carboxy-4,12-dibromo[2.2]paracyclophane from ester 4,12-dibromo-7-methoxycarbonyl[2.2]paracyclophane (4.3 g, 10.14 mmol) was refluxed for 16 hours in MeOH/$H_2O$ in presence of an excess of LiOH. The crude product so obtained was purified by washing the crude material with $Et_2O$/hexane to give 3.40 g (82% yield) of 7-carboxy-4,12-dibromo[2.2]paracyclophane.

f) Preparation of 7-carboxy-4,12-dibromo[2.2]paracyclophane[(S)-1-phenylethyl]amide from acyl chloride

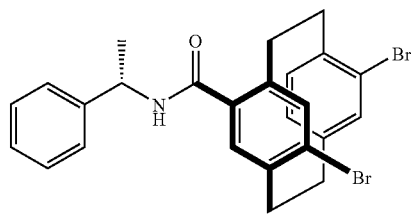

A solution of 7-chloroformyl-4,12-dibromo[2.2]paracyclophane (2 mmol) in dichloromethane (10 mL) was treated with (S)-(−)-α-methylbenzylamine (5 mmol) and stirred at room temperature for 1 h. The reaction was then treated with 2.8 M $NH_4Cl$ and extracted with dichloromethane. The combined organic phases were washed with $H_2O$ and saturated aqueous $NaHCO_3$, dried over anhydrous $MgSO_4$ and concentrated under vacuum to afford 715 mg (70% yield) of a 1:1 mixture of (R)-7-carboxy-4,12-dibromo[2.2]paracyclophane[(S)-1-phenylethyl]amide and (S)-7-carboxy-4,12-dibromo[2.2]paracyclophane[(S)-1-phenylethyl]amide.

Both diastereoisomers were separated by chromatographic column ($SiO_2$, from hexane/ethyl acetate 20:1 to hexane/ethyl acetate 3:1). $1^{st}$ eluting isomer (315 mg, 31% yield): $^1$H NMR ($CDCl_3$): 1.49 (d, 3H, J=6.9 Hz, NHCHCH$_3$), 2.6-2.8 (m, 1H), 2.8-3.1 (m, 4H), 3.2-3.4 (m, 2H), 3.42 (dd, 1H, J=12.4, 10.0 Hz), 5.19 (quint, 1H, J=7.3 Hz, NHCHCH$_3$), 5.70 (d, 1H, J=7.6 Hz, CONH), 6.32 (dd, 1H, J=7.8, 1.6 Hz, Ar—H), 6.59 (s, 1H, Ar—H), 6.74 (d, 1H, J=7.8 Hz, Ar—H), 7.11 (d, 1H, J=1.6 Hz, Ar—H), 7.13 (s, 1H, Ar—H), 7.2-7.3 (m, 1H, Ph—H), 7.3-7.4 (m, 4H, Ph—H) ppm. $2^{nd}$ eluting isomer (300 mg, 29% yield). $^1$H NMR ($CDCl_3$): 7.4-7.3 (m, 4H, Ph—H), 7.3-7.2 (m, 1H, Ph—H), 7.10 (d, 1H, J=1.7 Hz, Ar—H), 7.08 (s, 1H, Ar—H), 6.75 (d, 1H, J=7.8 Hz, Ar—H), 6.64 (s, 1H, Ar—H), 6.36 (dd, 1H, J=7.8, 1.7 Hz, Ar—H), 5.72 (d, 1H, J=7.7 Hz, CONH), 5.18 (quint, 1H, J=7.3 Hz, NHCHCH$_3$), 3.4-3.3 (m, 1H), 3.3-3.1 (m, 2H), 3.0-2.9 (m, 2H), 2.9-2.7 (m, 2H), 2.7-2.6 (m, 1H), 1.49 (d, 3H, J=6.9 Hz, NHCHCH$_3$) ppm.

g) Resolution of racemic 7-carboxy-4,12-dibromo[2.2]paracyclophane

A suspension of racemic 7-carboxy-4,12-dibromo[2.2] paracyclophane (4.29 g, 10.5 mmol) in EtOH (30 mL) was treated with a solution of (−)cinchonidine (3.08 mg, 10.5 mmol) in EtOH (30 mL), heated at 90° C. for 1 h and stirred at room temperature for an additional 2 h. The precipitated white crystalline solid (3.15 g, 4.5 mmol) was then filtered and identified as the cinchonidium salt of (S)-acid in 87% ee. The mother liquids contained 4.10 g of the cinchonidium salt of (R)-acid in 39% ee. The obtained solid was dissolved in EtOH (45 mL) at 90° C. and let stand over night at room temperature. Again, a white crystalline precipitate (1.9 g, 2.7 mmol) was formed and identified after filtration as the cinchonidium salt of (S)-acid in 97% ee (51% recovery of the (S)-acid enantiomer in 97% ee). Diastereomeric mixture: $^1$H NMR ($CDCl_3$): 1.65 (brs, 1H×2), 1.8-2.0 (m, 3H×2), 2.4-2.6 (m, 2H×2), 2.7-3.1 (m, 6H×2), 3.1-3.4 (m, 4H×2), 3.92 (q, 1H×2, J=11.0 Hz), 4.19 (brs, 1H×2), 4.89 (d, 1H×2, J=10.4 Hz), 4.94 (d, 1H×2, J=17.2 Hz), 5.51 (ddd, 1H×2, J=17.2, 10.4, 7.1 Hz), 6.15 (s, 1H×2), 6.19 (d, 1H, J=7.8 Hz, Ar—H), 6.32 (d, 1H, J=7.8 Hz, Ar—H), 6.55 (d, 1H, J=7.8 Hz, Ar—H), 6.56 (d, 1H, J=7.8 Hz, Ar—H), 6.91 (s, 1H×2, Ar—H), 6.95 (s, 1H, Ar—H), 6.99 (s, 1H, Ar—H), 7.04 (brs, 1H×2, Ar—H), 7.30 (t, 1H×2, J=7.5, Ar—H), 7.5-7.6 (m, 2H×2, Ar—H), 7.89 (d, 1H×2, J=8.4 Hz, Ar—H), 8.00 (d, 1H×2, J=8.4 Hz, Ar—H), 8.79 (d, 1H×2, J=4.5 Hz, Ar—H) ppm. Salt from (S)-enantiomer of the carboxylic acid: $^1$H NMR ($CDCl_3$): 1.66 (brs, 1H), 1.9-2.1 (m, 3H), 2.2-2.3 (m, 1H), 2.50 (brs, 1H), 2.6-2.8 (m, 3H), 2.9-3.4 (m, 7H), 3.81 (t, 1H, J=11.0 Hz), 4.23 (brs, 1H), 4.87 (d, 1H, J=10.4 Hz), 4.92 (d, 1H, J=17.2 Hz), 5.46 (ddd, 1H, J=17.2, 10.4, 7.1 Hz), 6.00 (s, 1H), 6.24 (d, 1H, J=7.5 Hz, Ar—H), 6.51 (d, 1H, J=7.7 Hz, Ar—H), 6.79 (s, 1H, Ar—H), 6.80 (s, 1H, Ar—H), 6.98 (brs, 1H, Ar—H), 7.24 (t, 1H, J=7.5, Ar—H), 7.5-7.6 (m, 2H, Ar—H), 7.85 (d, 1H, J=8.4 Hz, Ar—H), 7.96 (d, 1H, J=8.4 Hz, Ar—H), 8.74 (d, 1H, J=4.3 Hz, Ar—H) ppm. $^{13}$C NMR ($CDCl_3$): 18.7 (t), 25.0 (t), 27.3 (d), 32.1 (t), 33.1 (t), 35.0 (t), 35.5 (t), 37.8 (d), 43.2 (t), 54.2 (t), 59.8 (d), 66.7 (d, CHOH), 116.7 (t, CHCH$_2$), 118.7 (d), 122.5 (d), 124.8 (s), 126.4 (s), 126.9 (d), 128.3 (d), 129.3 (d), 130.1 (d), 131.2 (d), 132.4 (d), 133.4 (s), 134.1 (d), 136.1 (s), 137.0 (d), 137.8 (s), 138.3 (d), 139.2 (s), 140.9 (s), 142.6 (s), 147.2 (s), 147.7 (s), 149.8 (d), 174.0 (s, CO) ppm. $[\alpha]_D$=+74.4 (CH$_2$Cl$_2$, c=12.6 mg/mL).

h) Analytical Method for Enantiomeric Excess Determination

A solution of 7-carboxy-4,12-dibromo[2.2]paracyclophane in CH$_2$Cl$_2$ was treated with a 2M solution of (trimethylsilyl)diazomethane in hexanes to form 4,12-dibromo-7-methoxycarbonyl[2.2]paracyclophane in situ. After removal of the solvents under reduced pressure, the reaction mixture was filtered through a plug of silica and analysed by HPLC (column Chiralcel OJ, solvent hexane, flow rate 1.5 mL/min, retention times: (R)-7-carboxy-4,12-dibromo[2.2] paracyclophane 8.7 min, (S)-7-carboxy-4,12-dibromo[2.2] paracyclophane 12.4 min).

EXAMPLE 4

Synthesis of hydroxymethyl[2.2]paracyclophane Derivatives and their ethers a) Preparation of (R)-4,12-dibromo-7-hydroxymethyl[2.2]paracyclophane, method 1.

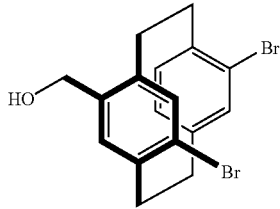

To a solution of (R)-4,12-dibromo-7-methoxycarbonyl [2.2]paracyclophane (424 mg, 1 mmol) in THF (5 mL) at 0° C. was slowly added LiAlH$_4$ (2 mL, 1 M solution in THF, 2 mmol). The reaction mixture was stirred at 0° C. for 30 min, let warm up to room temperature for an extra 30 min, cooled down again to 0° C., and quenched by slow addition of a 10:1 mixture MeOH/H$_2$O (5 mL). After warming up to room temperature, MgSO$_4$ was added to absorb the excess of H$_2$O, the mixture was then filtered to eliminate the aluminium and magnesium salts and concentrated under vacuum to afford the product (356 mg, 90% yield) as a white solid (mp=118.4° C.).

$^1$H NMR (CDCl$_3$): 2.6-2.8 (m, 2H), 2.8-3.0 (m, 3H), 3.1-3.2 (m, 1H), 3.34 (q, 2H, J=13.1 Hz), 4.31 (d, 1H, J=13.0 Hz, CH$_2$OH), 4.58 (d, 1H, J=13.0 Hz, CH$_2$OH), 6.35 (d, 1H, J=7.8 Hz), 6.43 (s, 1H), 6.56 (d, 1H, J=7.8 Hz), 7.10 (s, 1H), 7.14 (s, 1H) ppm. $^{13}$C NMR (CDCl$_3$): 29.9 (t), 32.1 (t), 34.4 (t), 35.3 (t), 63.4 (t), 125.5 (s), 126.8 (s), 131.2 (d), 131.4 (d), 133.1 (d), 133.8 (d, 2C), 138.4 (s), 138.8 (s), 139.1 (s), 139.8 (s), 141.1 (s) ppm. (R)-4,12-dibromo-7-hydroxymethyl[2.2] paracyclophane: $[\alpha]_D$=−139.7 (CH$_2$Cl$_2$, c=9.95 mg/mL).

b) Preparation of 4,12-dibromo-7-hydroxymethyl[2.2]paracyclophane, method 2

Borane-dimethyl sulfide complex (solution 2M in THF, 7.5 mL, 15 mmol) was added dropwise at room temperature to a THF (15 mL) solution of 7-carboxy-4,12-dibromo[2.2] paracyclophane (1.78 g, 4.34 mmol) (CAUTION! Violent reaction!). The reaction was heated to 45° C. for 30 minutes, then stirred at room temperature for 14 hours. The reaction was concentrated under reduced pressure to about 5 mL and CH$_2$Cl$_2$(50 mL) was added. The organic phase is washed with HCl$_2$N (2×50 mL) and NaHCO$_3$ saturated solution (50 mL), then dried over an. Na$_2$SO$_4$ and evaporated. The product was re-dissolved in MTBE (50 mL), washed with brine (2×50 mL), then dried over Na$_2$SO$_4$ and evaporated to give the product as a colourless oil that solidified upon standing overnight at room temperature (1.66 g, 96% yield). The reaction was repeated on various batches of racemic and enantiopure materials and achieved yields of 94-100%.

c) Preparation of 4,12-dibromo-7-(triisopropylsilyioxy)methyl[2.2]paracyclophane

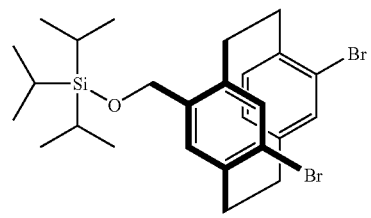

Lutidine (0.97 mL, 8.4 mmol) was added to a dichloromethane (25 mL) solution of 4,12-dibromo-7-hydroxymethyl[2.2]paracyclophane (1.66 g, 4.19 mmol), then triisopropylsilyltriflate (1.21 mL, 4.5 mmol) was added dropwise over 5 minutes at room temperature. The reaction was stirred at room temperature for one hour, then the solvent was concentrated under reduced pressure to about 5 mL and HCl 2N (50 mL) was added. The reaction was extracted with MTBE (2×50 mL). The combined organic layers were washed with brine (40 mL), dried over Na$_2$SO$_4$ and evaporated to give the product as a pale yellow oil that solidified upon standing at room temperature (1.95 g, 84% yield, mp=96.8° C.). $^1$H NMR (CDCl$_3$): 1.05-0.95 (6 lines, 18H, CH—CH$_3$), 1.1 (m, 3H, Si—CH), 2.6-2.8 (m, 2H, CH$_2$), 2.8-2.9 (m, 2H, CH$_2$), 2.9-3.1 (m, 2H, CH$_2$), 3.3-3.4 (m, 2H, CH$_2$), 3.34 (q, 2H, J=15 Hz, CH$_2$OH), 4.45 (d, 1H, J=15 Hz, CH$_2$OH), 4.65 (d, 1H, J=13.0 Hz, CH$_2$OH), 6.32 (d, 1H, J=8 Hz), 6.56 (s, 1H), 6.64 (d, 1H, J=8 Hz), 7.03 (s, 1H), 7.16 (s, 1H) ppm. $^{13}$C NMR (CDCl$_3$): 12.0 (CH—CH$_3$), 18.0 (CH—CH$_3$), 29.8 (CH$_2$), 32.1 (CH$_2$), 34.2 (CH$_2$), 35.5 (CH$_2$), 63.2 (CH$_2$—O), 124.6 (C), 126.7 (C), 131.31 (CH), 131.33 (CH), 132.7 (CH), 133.05 (CH), 133.2 (CH), 137.6 (C), 138.3 (C), 138.7 (C), 140.3 (C), 141.2 (C) ppm. (S)-4,12-dibromo-7-(triisopropylsilyloxy)methyl[2.2]paracyclophane: $[\alpha]_D$=94.17 (CH$_2$Cl$_2$, c=9.85 mg/mL). The reaction was repeated on different batches of racemic and enantiopure starting material (yields 82-94%).

d) Preparation of 4,12-dibromo-7-(triphenylmethoxy)methyl[2.2]paracyclophane

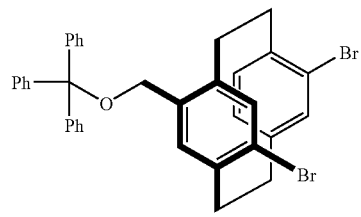

Method 1: A mixture of 4,12-dibromo-7-hydroxymethyl[2.2]paracyclophane (396 mg, 1 mmol), DMAP (12 mg, 0.1 mmol) and trityl bromide (388 mg, 1.2 mmol) in pyridine (5 mL) was stirred at room temperature for 48 hours. The reaction mixture was then diluted with MTBE, washed with 2.8M NH$_4$Cl, H$_2$O and saturated aqueous NaHCO$_3$, dried (an MgSO$_4$) and concentrated under vacuum to afford a residue that was purified by flash chromatography (SiO$_2$, 10% AcOEt in hexane) to yield the product (415 mg, 65% yield) as a white solid (mp=201.3° C.).

Method 2: Trityl chloride (659 mg, 2.36 mmol) was added in one portion to a solution of 4,12-dibromo-7-hydroxymethyl[2.2]paracyclophane (780 mg, 1.97 mmol) and DBU (0.4 mL, 2.76 mmol) in CH$_2$Cl$_2$ (7 mL) at room temperature. After stirring for 16 hours the reaction was quenched by addition of 10% HCl (10 mL), extracted with CH$_2$Cl$_2$, washed with saturated aqueous NaHCO$_3$ and saturated aqueous NaCl, dried (MgSO$_4$) and concentrated under vacuum to afford a residue that was purified by flash chromatography (hexane/ethyl acetate 20:1) to yield the product (1140 mg, 91% yield) as a white solid.

$^1$H NMR (CDCl$_3$): 2.11 (dt, 1H. J=13.6, 8.4 Hz), 2.6-2.8 (m, 2H), 2.8-3.1 (m, 4H), 3.38 (dd, 1H, J=11.7, 11.2 Hz), 3.77 (d, 1H, J=12.2 Hz, CH$_2$OTr), 3.99 (d, 1H, J=12.2 Hz, CH$_2$OTr), 6.02 (d, 1H, J=7.8 Hz), 6.22 (d, 1H, J=7.8 Hz), 6.65 (s, 1H), 7.04 (s, 1H), 7.08 (s, 1H), 7.22 (d, 3H, J=8.0 Hz, OTr), 7.29 (t, 6H, J=8.0 Hz, OTr), 7.46 (d, 6H, J=8.0 Hz, OTr) ppm. $^{13}$C NMR (CDCl$_3$): 29.9 (t), 32.1 (t), 33.9 (t), 35.4 (t), 63.7 (t), 86.9 (s), 124.9 (s), 126.7 (s), 127.2 (d, 3C, OTr), 128.0 (d, 6C, OTr), 128.7 (d, 6C, OTr), 131.0 (d), 131.1 (d), 133.0 (d), 133.4 (d), 135.5 (d), 138.1 (s), 138.2 (s), 138.7 (s), 138.8 (s), 141.0 (s), 143.8 (d, 3C, OTr) ppm. (S)-4,12-dibromo-7-(triphenylmethoxy)methyl[2.2]paracyclophane: [α]$_D$=68.33 (CH$_2$Cl$_2$, c=6.09 mg/mL).

e) Preparation of (R)-4,12-dibromo-7-(1-hydroxy-1-methylethyl)[2.2]paracyclophane

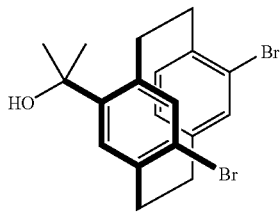

To a solution of 4,12-dibromo-7-methoxycarbonyl[2.2]paracyclophane (424 mg, 1 mmol) in THF (5 mL) at −78° C. was slowly added methylmagnesium bromide (3 mL, 1M solution in butyl ether, 3 mmol). The reaction mixture was stirred at −78° C. for 1 h, let warm up to room temperature for an extra hour, cooled down to 0° C., and quenched by slow addition of HCl 2N (5 mL). The reaction was then extracted with MTBE (2×10 mL). The combined organic layers were washed with brine (20 mL), dried over Na$_2$SO$_4$ and evaporated to give the product (424 mg, quantitative yield) as a white solid. $^1$H NMR (CDCl$_3$): 1.37 (s, 3H, CH$_3$), 1.57 (s, 3H, CH$_3$), 2.6-2.7 (m, 1H), 2.8-3.1 (m, 4H), 3.2-3.4 (m, 2H), 3.5-3.6 (m, 1H), 6.29 (d, 1H, J=7.9 Hz), 6.47 (s, 1H), 6.58 (d, 1 H, J=7.9 Hz), 6.98 (s,1H), 7.26 (s,1H) ppm.

EXAMPLE 5

Synthesis of hydroxy[2.2]paracyclophane Derivatives and their ethers a) Preparation of (R)-4,12-dibromo-7-formyl[2.2]paracyclophane

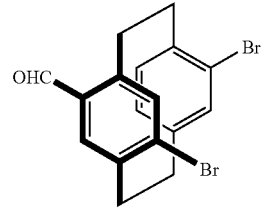

A solution of (R)-4,12-dibromo[2.2]paracyclophane (848 mg, 2.3 mmol) in CH$_2$Cl$_2$ (16 mL) at 0° C. was subsequently treated with TiCl$_4$ (4 mL, 1 M solution in CH$_2$Cl$_2$, 4.0 mmol) and Cl$_2$CHOMe (1.9 mL, 2.1 mmol). After stirring at 0° C. for 1 hour and at room temperature for 16 hours, the mixture was poured into ice and stirred for an additional hour. The reaction mixture was then extracted with CH$_2$Cl$_2$ and the combined organic phases were washed with saturated aqueous NaHCO$_3$ and brine, dried over Na$_2$SO$_4$ and evaporated. The obtained crude was then purified by column chromatography (hexane/ethyl acetate 10:1) to afford 763 mg of (R)-4,12-dibromo-7-formyl[2.2]paracyclophane (85% yield) as a white solid.

Alternatively, over night treatment of (S)-4,12-dibromo-7-hydroxymethyl[2.2]paracyclophane (396 mg, 1.0 mmol) in CH$_2$Cl$_2$ (5 mL) with MnO2 (869 mg, 10.0 mmol) afforded (S)-4,12-dibromo-7-formyl[2.2]paracyclophane (377 mg, 96% yield) after filtering the reaction mixture through celite and evaporating the solvents under reduced pressure (mp=128.0° C.). $^1$H NMR (CDCl$_3$): 2.7-2.9 (m, 2H), 2.9-3.1 (m, 3H), 3.3-3.5 (m, 2H), 3.79 (dd, 1H, J=13.0, 9.9 Hz), 6.33 (d, 1H, J=7.8 Hz), 6.36 (dd, 1H, J=7.8, 1.5 Hz), 6.95 (s, 1H), 7.08 (d, 1H, J=1.5 Hz), 7.23 (s, 1H), 9.82 (s, 1H, CHO) ppm. $^{13}$C NMR (CDCl$_3$): 30.4(t), 32.2 (t), 35.3 (t), 35.7 (t), 126.8 (s), 131.0 (d), 132.8 (d), 133.0 (s), 133.9 (d), 135.3 (d), 136.1 (s), 137.8 (d), 138.7 (s), 140.0 (s), 141.1 (s), 144.1 (s), 190.9 (s, COH) ppm. [α]$_D$=−126.7 (CH$_2$Cl$_2$, c=5.67 mg/mL).

b) Preparation of (R)-4,12-dibromo-7-hydroxy[2.2]paracyclophane

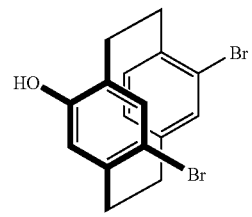

3-Chloroperbenzoic acid (501 mg, 75% max purity, 2.9 mmol) was added in portions to a solution of (R)-4,12-dibromo-7-formyl[2.2]paracyclophane (763 mg, 1.94 mmol) in CH$_2$Cl$_2$ (12 mL) at room temperature. After stirring overnight, the reaction mixture was cooled to 0° C. and the precipitated 3-chlorobenzoic acid was filtered off. The organic solution was then washed with saturated aqueous NaHCO$_3$, dried over Na$_2$SO$_4$ and evaporated. The crude, identified as (R)-4,12-dibromo-7-formyloxy[2.2]paracyclophane, was dissolved in MeOH (12 mL), treated with a 2M solution of NaOH (5 mL) and stirred at room temperature for 30 minutes. Once the hydrolysis reaction is completed, the reaction mixture was extracted with MTBE, washed with 10% HCl and brine, dried over $Na_2SO_4$ and evaporated. The obtained crude was then purified by column chromatography ($SiO_2$, hexane/ethyl acetate 5:1) to afford 570 mg (R)-4,12-dibromo-7-hydroxy[2.2]paracyclophane in 75% yield as a white solid. $^1$H NMR ($CDCl_3$): 2.57 (ddd, 1H, J=13.1, 10.4, 6.4 Hz), 2.78 (ddd, 1H, J=13.1, 9.8, 7.3 Hz), 2.8-3.1 (m, 4H), 3.2-3.3 (m, 2H), 4.58 (brs, 1H, OH), 5.62 (s, 1H), 6.38 (dd, 1H, J=7.8, 1.4 Hz), 6.92 (d, 1H, J=7.8 Hz), 7.06 (s, 2H) ppm. $^{13}$C NMR ($CDCl_3$): 28.3 (t), 32.4 (t), 33.9 (t), 35.2 (t), 117.3 (s), 123.6 (s), 127.2 (s), 127.4 (s), 130.7 (d), 130.9 (d), 133.7 (d), 134.1 (d), 139.0 (s), 140.4 (s), 140.7 (s), 153.9 (s) ppm. $[\alpha]_D$=−101.2 ($CH_2Cl_2$, c=9.9 mg/mL).

c) Preparation of (R)-4,12-dibromo-7-methoxy[2.2]paracyclophane

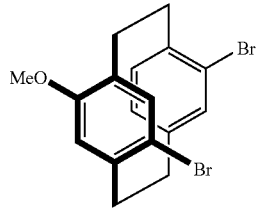

A solution of (R)-4,12-dibromo[2.2]paracyclophan-7-ol (563 mg, 1.47 mmol) in THF (5 mL) was slowly added to a suspension of NaH (65 mg, 60% in mineral oil, 1.62 mmol) in THF (10 mL) at room temperature. After stirring for 5 minutes, iodomethane (135 □L, 2.2 mmol) was slowly added and the reaction mixture was stirred 16 hours at room temperature. After evaporating the solvents under reduced pressure, the crude was dissolve in MTBE and washed with 1M NaOH, 10% HCl and brine, dried over $Na_2SO_4$ and evaporated. The crude was purified by column chromatography ($SiO_2$, hexane/ethyl acetate 20:1) to afford 514 mg of (R)-4,12-dibromo-7-methoxy[2.2]paracyclophane (88% yield) as a white solid (mp=118.2° C.). $^1$H NMR ($CDCl_3$): 2.66 (ddd, 1H, J=13.2, 11.5, 6.2 Hz), 2.71 (ddd, 1H, J=13.7, 9.7, 7.3 Hz), 2.8-3.0 (m, 2H), 2.99 (ddd, 1H, J=13.0, 10.2, 6.2 Hz), 3.12 (dd, 1H, J=12.7, 9.7 Hz), 3.20 (dd, 1H, J=13.0, 10.2 Hz), 3.31 (ddd, 1H, J=12.3, 10.2, 2.0 Hz), 3.62 (s, 3H, $OCH_3$), 5.70 (s, 1H), 6.37 (dd, 1H, J=7.8, 1.7 Hz), 6.67 (d, 1H, J=7.8 Hz), 7.03 (d, 1H, J=1.7 Hz), 7.07 (s, 1H) ppm. $^{13}$C NMR ($CDCl_3$): 28.5 (t), 32.4 (t), 34.0 (t), 35.6 (t), 54.6 (q, $OCH_3$), 116.9 (s), 117.8 (d), 127.3 (s), 128.7 (s), 130.5 (d), 130.7 (d), 133.7 (d, 2C), 139.5 (s), 140.2 (s), 140.4 (s), 157.6 (s) ppm. $[\alpha]_D$=−125.6 ($CH_2Cl_2$, c=11.53 mg/mL).

EXAMPLE 6

Synthesis of Phosphine Ligands Based on [2.2]paracyclophane Derivatives a) Preparation of (R)-4,12-bis(diphenylphosphino)-7-(triphenylmethoxy)methyl[2.2]paracyclophane ("TriOCH$_2$-ParaC")

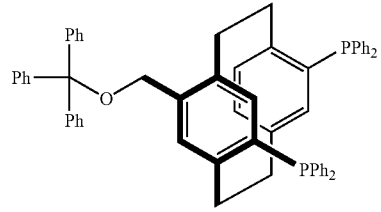

To a solution of (R)-4,12-dibromo-7-(triphenylmethoxy)methyl[2.2]paracyclophane (638 mg, 1 mmol) in THF (5 mL) at −78° C. was slowly added t-BuLi (2.5 mL, 1.7 M in pentane, 4.2 mmol) and the coloured mixture was stirred at this temperature for 30 minutes. The cooling bath was then removed and a mixture of chlorodiphenylphosphine (0.5 mL, 2.2 mmol) in THF (3 mL) was added drop-wise. The yellow solution was stirred for 1 hour, treated with $SiO_2$ and stirred for an extra 30 min. The $SiO_2$ was filtered off and washed with $CH_2Cl_2$. The solvents were removed under vacuum and the residue was dissolved in $CH_2Cl_2$, filtered to eliminate the LiCl formed during the reaction and triturated by addition of hexane. After stirring the mixture for 1 hour, the precipitated product was collected by filtration (680 mg, 80% yield). $^1$H NMR ($CDCl_3$): 7.5-7.0 (m, 35H, OTr+$PPh_2$), 6.70 (d, 1H, J=5.3 Hz), 6.55 (d, 1H, J=9.0 Hz), 6.42 (d, 1H, J=9.0 Hz), 6.29 (d, 1H, J=7.7 Hz), 6.08 (dd, 1H, J=7.7, 5.3 Hz), 4.06 (d, 1H, J=12.2 Hz, $CH_2OTr$), 3.90 (d, 1H, J=12.2 Hz, $CH_2OTr$), 3.0-2.5 (m, 7H), 2.0-1.9 (m, 1H) ppm. $^{31}$P NMR ($CDCl_3$): −1.18, −1.24 ppm.

b) Preparation of rac-4,12-bis(diphenylphosphino)-7-(triisopropylsilyloxy)-methyl[2.2]paracyclophane ("TIPSO—CH-ParaC")

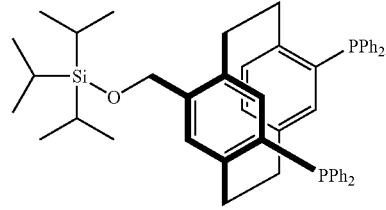

To a diethyl ether (17 mL) solution of 4,12-dibromo-7-(tris-isopropylsilyloxy)methyl[2.2]paracyclophane (555 mg, 1 mmol) at −78° C. was slowly added t-BuLi (2.35 mL, 1.7M in pentane, 4 mmol) and the coloured solution was stirred at −78° C. for one hour. The reaction was quenched by adding chlorodiphenylphosphine (0.45 mL, 2.5 mmol) at −78° C. The colour immediately changed from orange to pale yellow. The cooling bath was removed, the reaction stirred at room temperature for 30 minutes and a white solid (LiCl) precipitated. The reaction was treated with $SiO_2$, stirred for further 30 minutes and then filtered under nitrogen. The solution was evaporated to give aple yellow solid that was deemed to be of sufficient purity (750 mg, quantitative yield). $^{31}$P NMR ($CDCl_3$): −1.2, −1.7 ppm.

c) Preparation of (R)-4,12-bis(diphenylphosphino)-7-(tris-isopropylsilyloxy)methyl-[2.2]paracyclophane ("TIPSO—CH$_2$-ParaC")

To a diethyl ether (20 mL) solution of (R)-4,12-dibromo-7-(tris-isopropylsilyloxy)methyl-[2.2]paracyclophane (556 mg, 1 mmol) at −78° C. was slowly added t-BuLi (2.4 mL, 1.7 M in pentane, 4.05 mmol) and the coloured solution was stirred at −78° C. for 40 minutes. The reaction was quenched by adding chlorodiphenylphosphine (0.45 mL, 2.5 mmol) at −78° C. The colour immediately changed from orange to pale yellow. The cooling bath was removed, the reaction stirred at room temperature for 100 minutes and a white solid (LiCl) precipitated. The reaction was treated with $SiO_2$, stirred for one hour and then filtered under nitrogen. The solution was evaporated and the solid residue was washed with methanol (5 mL) and diethyl ether (5 mL). After further washing with methanol (5 mL) the resulting white solid (mp=170.6° C.) was dried under vacuum (420 mg, 55% yield). $^1$H NMR ($CDCl_3$): 1.0-1.15 (m, 21H, TIPS-O), 2.4-2.6 (m, 2H, CH$_2$), 2.8-3.0 (m, 6H, CH$_2$), 4.6 (d, 1H, J=15 Hz, CH$_2$—O), 4.7 (d, 1H, J=15 Hz, CH$_2$—O), 6.35-6.45 (4 lines, 2H, H arom), 6.55-6.65 (m, 3H, H arom), 7.05-7.50 (m, 20H, H arom). $^{31}$P NMR (CDCl$_3$): −1.2, −1.7 ppm. [α]$_D$=−25.5 (CH$_2$Cl$_2$, c=10.57 mg/mL).

d) Preparation of (S)-4,12-bis[bis(3,5dimethylphenyl)phosphino]-7-(tris-isopropylsilyloxy)methyl-[2.2]paracyclophane ("TIPSO—CH$_2$-Xyl-ParaC")

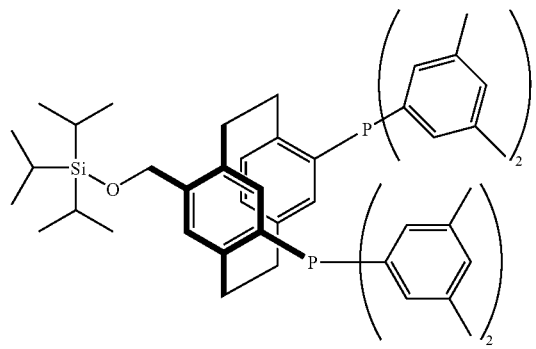

To a diethyl ether (20 mL) solution of (S)-4,12-dibromo-7-(tris-isopropylsilyloxy)methyl[2.2]paracyclophane (276 mg, 0.5 mmol) at −78° C. was slowly added t-BuLi (1.23 mL, 1.7 M in pentane, 2.1 mmol) and the coloured solution was stirred at −78° C. for 45 minutes. The reaction was quenched by adding a diethyl ether (6 mL) solution chloro-bis-(3,5-dimethylphenyl)phosphine (0.33 g, 1.2 mmol) at −78° C. The cooling bath was removed, the reaction stirred at room temperature for one hour and a white solid (LiCl) precipitated. The reaction was treated with SiO$_2$, stirred for one hour and then filtered under nitrogen. The solvent was evaporated, the solid residue was re-dissolved in 10 mL of toluene/hexane 2/3 and eluted through a 2 cm silica gel plug. The solvent was removed under vacuum to give the product as a white solid (110 mg, 25% yield, mp=160.1° C.). $^1$H NMR (CDCl$_3$): 1.0-1.10 (m, 21H, TIPS-O), 2.1 (s, 12H, 4 CH$_3$), 2.2 (s, 6H, 2 CH$_3$), 2.25 (s, 3H, CH$_3$), 2.27 (s, 3H, CH$_3$), 2.35-2.55 (m, 2H, CH$_2$), 2.7-2.9 (m, 6H, CH$_2$), 4.55 (d, 1H, J=14 Hz, CH$_2$—O), 4.7 (d, 1H, J=14 Hz, CH$_2$—O), 6.30 (dd, 1H, H arom), 6.47 (4 lines, 2H, H arom), 6.59 (m, 2H, H arom), 6.7-7.2 (m, 12H, H arom). $^{31}$P NMR (CDCl$_3$): 0.3, −0.3 ppm.

e) Preparation of (S)-4,12-bis[bis(3.5-dimethyl-4-methoxyphenyl)phosphino]-7-(tris-isopropylsilyloxy)methyl[2.2]paracyclophane ("TIPSO—CH$_2$-MeOXyl-ParaC")

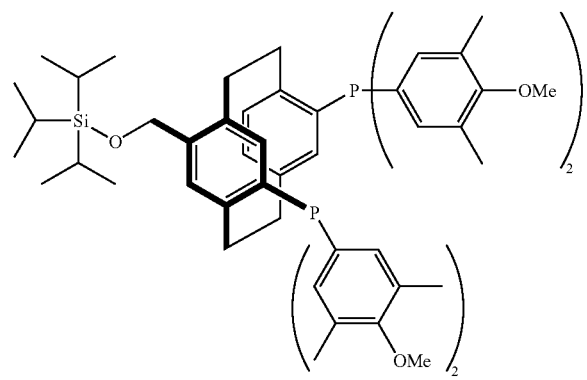

To a diethyl ether (15 mL) solution of (S)-4,12-dibromo-7-(tris-isopropylsilyloxy)methyl[2.2]paracyclophane (185 mg, 0.34 mmol) at −78° C. was slowly added t-BuLi (0.82 mL, 1.7 M in pentane, 1.4 mmol) and the coloured solution was stirred at −78° C. for 45 minutes. The solution containing the dianion was added dropwise to a diethyl ether (8 mL) solution chloro-bis-(3,5-dimethy-4-methoxylphenyl)phosphine (0.24 g, 0.72 mmol) at room temperature. The reaction was stirred at room temperature for two hours and a white solid (LiCl) precipitated. The reaction was treated with SiO$_2$, stirred for three hours and then filtered under nitrogen. The solvent was evaporated and the crude product was used without any further purification (see below, example h). $^{31}$P NMR (CDCl$_3$): −2, −3 ppm.

f) Preparation of rac-4,12-bis(diphenylphosphino)-7-hydroxymethyl[2.2]paracyclophane ("HO—CH$_2$-ParaC")

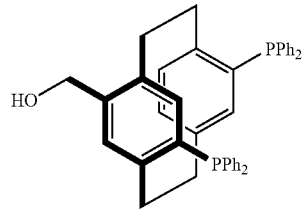

etrabutylammonium fluoride (1.2 mL, 1 M solution in THF+5% water) was added to a THF 15 mL) solution of rac-4,12-bis(diphenylphosphino)-7-(triphenylmethoxy)-methyl[2.2]paracyclophane (866 mg, 1.14 mmol) and the reaction was stirred at room temperature for one hour. The solvent was evaporated and degasses diethyl ether (50 mL) was added. The ether solution was washed with water (50 mL), HCl 2N (50 mL) and NaHCO$_3$ sat solution (50 mL), then dried over Na$_2$SO$_4$, filtered under nitrogen and evaporated. The resulting pale yellow solid residue was washed with diethyl ether (1 mL) and hexane (5 mL) and dried to give the product as a off white solid (410 mg, 60% yield).

g) Preparation of (R)-4,12-bis(diphenylphosphino)-7-hydroxymethyl[2.2]paracyclophane ("HO—CH$_2$-ParaC")

Tetrabutylammonium fluoride (1.0 mL, 1 M solution in THF+5% water, 1 mmol) was added to a THF (10 mL) solution of (R)-4,12-bis(diphenylphosphino)-7-(triphenylmethoxy)methyl[2.2]paracyclophane (650 mg, 0.85 mmol) and the reaction was stirred at room temperature for two hours. The solvent was evaporated and diethyl ether (50 mL) was added. The ether solution was washed with water (20 mL), HCl 2N (20 mL) and NaHCO$_3$ sat solution (20 mL), then dried over Na$_2$SO$_4$, filtered under nitrogen and evaporated. The resulting pale yellow solid residue was washed with pentane (2×10 mL) and dried to give the product as a off white solid (450 mg, 70% yield). $^1$H NMR (CDCl$_3$): 2.4-2.5 (m, 2H, CH$_2$), 2.7-3.0 (m, 6H, CH$_2$), 4.32 (d, 1H, J=14 Hz, CH$_2$—O), 4.6 (d, 1H, J=14 Hz, CH$_2$—O), 6.30-6.35 (m, 2H, H arom), 6.4-6.5 (m, 3H H arom), 7.0-7.4 (m, 20H, H arom). $^{31}$P NMR (CDCl$_3$): −1.1, −1.3 ppm.

h) Preparation of (S)-4,12-bis[bis(3,5-dimethyl-4-methoxyphenyl)phosphino]hydroxymethyl[2.2]paracyclophane ("HO—CH$_2$-MeOXylParaC")

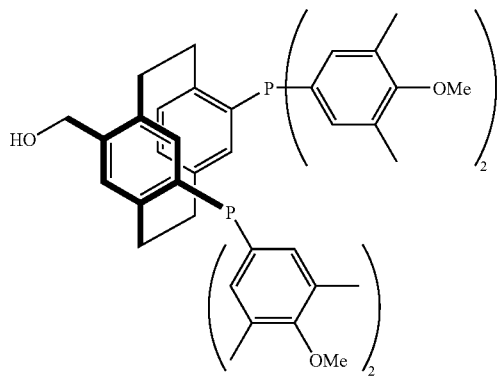

A tetrahydrofuran solution of tetrabutyl ammonium fluoride (0.4 mL, 1 M solution, 0.4 mmol) was added to a tetrahydrofuran (5 mL) solution of the crude product obtained in example 6e). The reaction was stirred at room temperature for two hours, then the solvent was evaporated. The solid residue was taken up in diethyl ether (20 mL) and, under inert atmosphere, washed with NaHCO$_3$ sat solution (10 mL) and HCl 2N (10 mL). The organic solution was dried over Na$_2$SO$_4$, filtered and evaporated. The crude product was purified by filtration over silica gel under inert atmosphere (eluent: toluene/diethyl ether 8/2). (75 mg, 29% yield+some impure fractions). $^{31}$P NMR (CDCl$_3$): −2.1, −2.4 ppm.

i) Preparation of rac-4,12-bis(diphenylphosphino)-7-tertbutoxycarbonyl[2.2]para cyclophane ("t-BuOOC-ParaC")

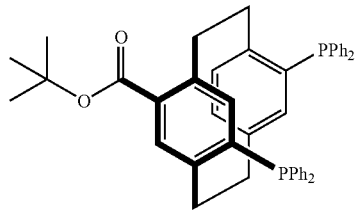

To a diethyl ether (20 mL) solution of rac-4,12-dibromo-7-tertbutoxycarbonyl[2.2]paracyclophane (358 mg, 0.77 mmol) at −78° C. was slowly added t-BuLi (1.85 mL, 1.7 M in pentane, 3.151 mmol) and the coloured solution was stirred at −78° C. for 40 minutes. The reaction was quenched by adding chloro-diphenylphosphine (0.3 mL, 1.7 mmol) at −78° C. The cooling bath was removed, the reaction stirred at room temperature for one hour and a white solid (LiCl) precipitated. The reaction was quenched with wet tertrahydrofuran (2 mL), diluted with more diethyl ether (20 mL) dried over Na$_2$SO$_4$ and filtered. The solvent was evaporated, the solid residue was washed with methanol (2×5 mL) and then dried under vacuum (320 mg, 47% yield). $^1$H NMR (CDCl$_3$): 1.5 (s, 9H, t-Bu—O), 2.55 (m, 1H, CH$_2$), 2.63 (m, 1H, CH$_2$), 2.8-3.0 (m, 5H, CH$_2$), 3.7 (m, 1H, CH$_2$), 6.4-6.55 (m, 3H, H arom), 7.05-7.55 (m, 22H H arom). $^{31}$P NMR (CDCl$_3$): −1.35 ppm.

j) Preparation of rac-4,12-bis(diphenylphosphino)-7-methoxy[2.2]paracyclophane ("MeO-Para-C")

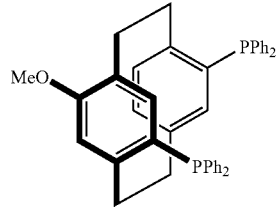

To a diethyl ether (15 mL) solution of rac-4,12-dibromo-7-methoxy[2.2]paracyclophane (133 mg, 0.335 mmol) at −78° C. was slowly added t-BuLi (0.8 mL, 1.7 M in pentane, 1.36 mmol) and the coloured solution was stirred at −78° C. for 90 minutes. The reaction was quenched by adding a diethyl ether (5 mL) solution chloro-diphenylphosphine (0.155 g, 0.7 mmol) at −78° C. The cooling bath was removed, the reaction stirred at room temperature for one hour and a white solid (LiCl) precipitated. The reaction was treated with SiO$_2$, stirred for one hour and then filtered under nitrogen. The solvent was evaporated, the solid residue was re-dissolved in 10 mL of toluene and eluted through a 2 cm silica gel plug. The solvent was removed under vacuum to give the product as a white solid of mp=173.3° C. (80 mg, 40% yield). $^1$H NMR (CDCl$_3$): 2.4-2.5 (m, 1H, CH$_2$), 2.7-2.85 (m, 4H, CH$_2$), 2.9-3.05 (m, 3H, CH$_2$), 3.69 (s, 3H, OCH$_3$), 5.78 (d, 1H, J=4.2 Hz, H arom), 6.42 (dd, 1H, J=7.7, 1.5 Hz, H arom), 6.4-6.5 (m, 2H, H arom), 6.65 (dd, 1H, J=7.7, 5.5 Hz H arom), 7.05-7.5 (m, 20H, H arom). $^{31}$P NMR (CDCl$_3$): −0.9, −3.0 ppm.

k) Preparation of (R)-4,12-bis(diphenylphosphino)-7-methoxy[2.2]paracyclophane ("CH$_3$—O-ParaC")

To a diethyl ether (15 mL) solution of (R)-4,12-dibromo-7-methoxy[2.2]paracyclophane (100 mg, 0.25 mmol) at −78° C. was slowly added t-BuLi (0.61 mL, 1.7 M in pentane, 1.0 mmol) and the coloured solution was stirred at −78° C. for 50 minutes. The reaction was quenched by adding a diethyl ether (5 mL) solution of chloro-diphenylphosphine (0.125 g, 0.55 mmol) at −78° C. The cooling bath was removed, the reaction stirred at room temperature for one hour and a white solid (LiCl) precipitated. The reaction was treated with SiO$_2$, stirred for one hour and then filtered under nitrogen. The solvent was evaporated, the solid residue was dissolved in dichloromethane (1 mL) and hexane (3 mL). Dichloromethane was removed under vaccum, the resulting solid precipitate was allowed to settle and the supernatant was removed. The procedure was repeated twice. The product was isolated as a white powder (63 mg, 41% yield). [α]$_D$=49.2 (CH$_2$Cl$_2$, c=1.16 mg/mL).

l) Preparation of rac-4,12-bis(diphenylphosphino)-7-t-butyldimethylsilyloxy[2.2]paracyclophane ("TBSO-ParaC")

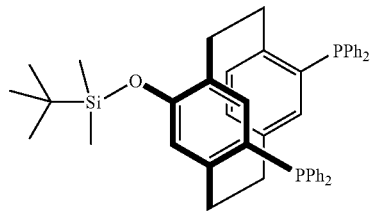

To a diethyl ether (10 mL) solution of rac-4,12-dibromo-7-t-butyldimethylsilyloxy[2.2]paracyclophane (90 mg, 0.18 mmol) at −78° C. was slowly added t-BuLi (0.44 mL, 1.7 M in pentane, 0.75 mmol) and the coloured solution was stirred at −78° C. for 50 minutes. The reaction was quenched by adding a diethyl ether (5 mL) solution chloro-diphenylphosphine (0.09 g, 0.4 mmol) at −78° C. The cooling bath was removed, the reaction stirred at room temperature for one hour and a white solid (LiCl) precipitated. The reaction was treated with $SiO_2$, stirred for one hour and then filtered under nitrogen. The solvent was evaporated, the product was obtained as a white solid (85 mg, 67% yield). $^1$H NMR ($CDCl_3$): 1.0 (s, 9H, t-BuSi), 1.08 (s, 3H, $CH_3Si$), 1.10 (s, 3H, $CH_3Si$), 2.4 (m, 1H, $CH_2$), 2.7-3.0 (m, 7H, $CH_2$), 5.70 (d, 1H, H arom), 6.4 (m, 2H, h arom), 6.5 (d, 1H, H arom), 6.9 (dd, 1H, H arom), 7.05-7.5 (m, 20H, H arom). $^{31}$P NMR ($CDCl_3$): −1.0, −2.35 ppm.

m) Preparation of 4,12-bis(diphenylphosphinooxide)-7-(triisopropylsilyloxy)methyl[2.2]para cyclophane

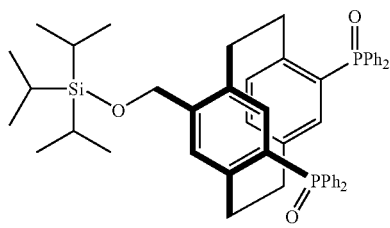

Pd(OAc)$_2$ (31 mg, 0.14 mmol), bis-diphenylphosphinobutane (60 mg, 0.14 mmol) and diphenylphosphine-oxide (200 mg, 1 mmol) were dissolved in anhydrous, degassed DMSO (2 mL) and the reaction heated to 115° C. After 5 minutes 4,12-dibromo-7-(tris-isopropylsilyloxy)methyl[2.2]paracyclophane (200 mg, 0.36 mmol) was added and the reaction was stirred at 115° C. for 16 hours. The solvent was evaporated, HCl 2N (50 mL) was added and the reaction was extracted with dichloromethane (3×50 mL). The combined organic layers were dried over $Na_2SO_4$, filtered and evaporated. The crude mixture was purified by chromatography ($SiO_2$, eluent: hexane/MTBE/dichloromethane 4/4/2) to give the product as a white powder (116 mg, 15% yield). ). $^1$H NMR ($CDCl_3$): 1.05 (t, 9 H, C$\underline{H}_3$—CH—Si J=8.5 Hz), 1.15 (m, 3H, $CH_3C\underline{H}Si$), 2.65 (m, 2H, —$CH_2$—), 2.9 (m, 2H, —$CH_2$—), 3.1 (m, 2H, —$CH_2$—), 3.3 (m, 2H, —$CH_2$—), 4.65 (d, 1H, —$CH_2$—O, J=6 Hz), 4.72 (d, 1H, —$CH_2$—O, J=6 Hz), 6.53 (d, 1H, H arom), 6.2 (d, 1H, H arom), 6.25 (m, 1H, H arom), 6.95 (d, 1H, H arom), 7.12 (d, 1H, H arom), 7.2 (m, 3H, H arom), 7.28 (m, 2H, H arom), 7.45 (m, 11H, H arom), 7.6 (m, 4H, H arom). $^{31}$P NMR ($CDCl_3$): 23.3, 22.9 ppm. This material can be reduced to the corresponding phosphine by treatment with $HSiCl_3$, $Et_3N$ in xylene at 120° C. NMR scale experiment: $^{31}$P NMR ($CDCl_3$): −1.2, −1.7 ppm.

EXAMPLE 7

Synthesis of Ruthenium Complexes of Phosphine Ligands Based on Substituted [2.2]paracyclophane Derivatives a) Preparation of [(R)-TriOCH$_3$-Para-C]RuCl$_2$[(S,S)-Dpen] '

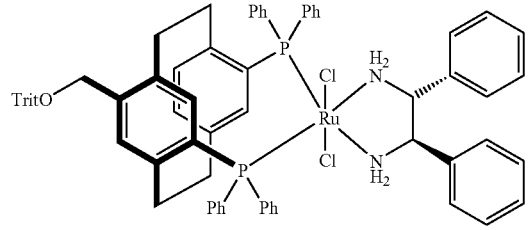

The phosphine of Example 6a ((R) enantiomer, 50 mg, 0.05889 mmol) and [Ru(benzene)Cl]$_2$ (14.7 mg, 0.0294 mmol) were placed in a Schlenk flask and the air was replaced with nitrogen. Anhydrous, degassed DMF (1.5 ml) and toluene (2 ml) were added. The mixture was then heated at 105° C. for 4 hours. A red homogeneous solution was obtained. To the solution was then added solid (S,S)-Dpen (12.5 mg, 0.05889 mmol) and the solution heated again for 1.75 hrs at 105° C. The solvent was then removed. The solid was dissolved in $CH_2Cl_2$ and MTBE added. Removal of the solvent caused precipitation of a tan coloured solid. The solid was not collected but the solvent completely removed to give the crude complex, which was used without any further purification. $^{31}$P NMR ($CDCl_3$): 43.98 ppm.

b) Preparation of [(S)-MeO-Para-C]RuCl$_2$[(R,R)-Dpen]

The phosphine ((S) enantiomer of Example 6j, 49 mg, 0.0807 mmol) and [Ru(benzene)Cl]$_2$ (20.2 mg, 0.0403 mmol) were placed in a Schlenk flask and the air was replaced with nitrogen. Anhydrous, degassed DMF (1 ml) and toluene (1 ml) were added. The mixture was then heated at 105° C. for 4 hours. To the solution was then added solid (S,S)-Dpen (17 mg, 0.0807 mmol) and the colour changed immediately from brown to yellow-beige. The reaction was allowed to cool to room temperature and the solvent was removed under vacuum. The crude complex was used without any further purification. $^{31}$P NMR ($CDCl_3$): 46.2 (d, J=28 Hz), 45.9 (d, 27.5 Hz) ppm.

c) Preparation of [(R)-TIPSOCH$_2$-Para-C]RuCl$_2$[(S,S)-Dpen]

The same procedure as used for example 7b was followed using the (R) enantiomer ligand of example 6c. The crude complex was used without any further purification. $^{31}$P NMR ($CDCl_3$): 43.6, 43.75, 43.8, 44.0 (not first order) ppm.

d) Preparation of [(R)-HOCH$_2$-Para-C]RuCl$_2$[(S,S)-Dpen]

The same procedure as used for example 7b was followed using the (R) enantiomer ligand of example 6g. The crude complex was used without any further purification. $^{31}$P NMR ($CDCl_3$): 44.0 (s) ppm.

EXAMPLE 8

Synthesis of Rhodium Complexes of Phosphine Ligands Based on [2.2]paracyclophane Derivatives a) Preparation of [(R)-TriOCH$_2$-ParaC Rh NBD]BF$_4$

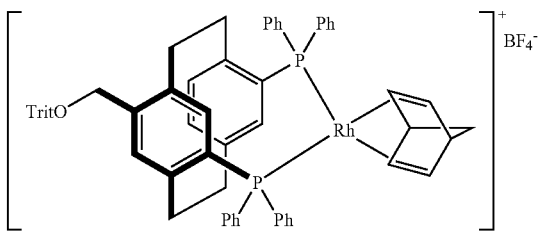

The phosphine of Example 6a ((R) enantiomer, 66 mg, 0.078 mmol) and [Rh(NBD)$_2$]BF$_4$ (27 mg, 0.072 mmol) (NBD=norbornadiene) were placed in Schlenk flask under inert nitrogen atmosphere and degassed dichloromethane (2 mL) was added at room temperature. The colour of the solution quickly turned from red to orange. After one hour the solvent was removed under vacuum and the crude solid residue was washed with Et$_2$O (1 mL) and hexane (2 mL). The yellow suspension was stirred for one hour, then the solid was allowed to settle and the supernatant liquid was removed. The solid was washed with more hexane and dried under vacuum (50 mg, 63% yield). The precatalyst was used without any further purification. $^{31}$P NMR (CDCl$_3$): 35.3 (dd, J$_{P—Rh}$=158 Hz, $^3$J$_{P—P}$=21 Hz), 37.4 (dd, J$_{P—Rh}$=159 Hz, $^3$J$_{P—P}$=21 Hz).

b) Preparation of [HO—CH$_2$-ParaC Rh NBD]BF$_4$

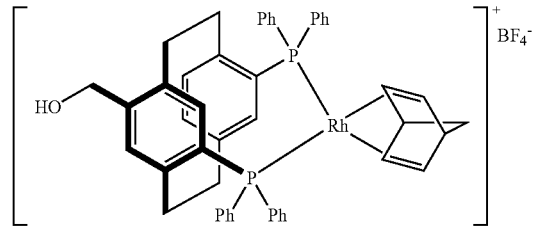

The (R)-enantiomer of the phosphine ligand of Example 6g (135 mg, 0.22 mmol) and [Rh(NBD)$_2$]BF$_4$ (75 mg, 0.2 mmol) (NBD=norbornadiene) were placed in Schlenk flask under inert nitrogen atmosphere and degassed CH$_2$Cl$_2$ (15 mL) was added at room temperature. The colour of the solution quickly turned from red to orange. After two hours the solvent was removed under vacuum and the crude solid residue was washed with diethyl ether (1 mL) and hexane (5 mL). The solid was allowed to settle and the supernatant liquid was removed and the solid dried under vacuum (145 mg, 81% yield). $^{31}$P NMR (CDCl$_3$): 35.2 (dd, J$_{P—Rh}$=158 Hz, $^3$J$_{P—P}$=21 Hz), 36.4 (dd, J$_{P—Rh}$=160 Hz, $^3$J$_{P—P}$=20 Hz).

c) Preparation of Rhodium Complexes: General Procedure

The appropriate ligand of Example 6 and an equimolar amount of [Rh(NBD)$_2$] were placed in Schlenk flask under inert nitrogen atmosphere and dichloromethane was added at room temperature. The colour of the solution quickly turned from red to orange. After 0.5-2 hours the solvent was removed under vacuum and the crude solid residue was analysed by $^{31}$P NMR. If deemed necessary the product was further purified by washing with diethyl ether and hexane, otherwise it was used without any further purification.

i) [(S)-TIPSO—CH$_2$-Xyl-Para-C Rh NBD]BF$_4$ (yield not calculated). $^{31}$P NMR (CDCl$_3$): 36.2 (dd, J$_{P—Rh}$=159 Hz, $^3$J$_{P—P}$=21 Hz), 37.1 (dd, J$_{P—Rh}$=159 Hz, $^3$J$_{P—P}$=21 Hz).

ii) [(S)-HO—CH$_2$-MeOXyl-Para-C Rh NBD]BF$_4$ (yield not calculated). $^{31}$P NMR (CDCl$_3$): 34.0 (dd, J$_{P—Rh}$=159 Hz, $^3$J$_{P—P}$=21 Hz), 36.0 (dd, J$_{P—Rh}$=159 Hz, $^3$J$_{P—P}$=21 Hz). [rac-tBuOOC-Para-C Rh NBD]BF$_4$ (yield not calculated). $^{31}$P NMR (CDCl$_3$): 35.9 (dd, J$_{P—Rh}$=159 Hz, $^3$J$_{P—P}$=23 Hz), 37.8 (dd, J$_{P—Rh}$=159 Hz, $^3$J$_{P—P}$=23 Hz).

iv) [rac-CH$_3$O-Para-C Rh NBD]BF$_4$ (83% yield) and [(R)-CH$_3$O-ParaC Rh NBD]BF$_4$ (yield not calculated). $^{31}$P NMR (CDCl$_3$): 34.1 (dd, J$_{P—Rh}$=157 Hz, $^3$J$_{P—P}$=21 Hz), 38.1 (dd, J$_{P—Rh}$=157 Hz, $^3$J$_{P—P}$=20 Hz).

v) [rac-TBSO-Para-C Rh NBD]BF$_4$ (98% yield). $^{31}$P NMR (CDCl$_3$): 34.9 (dd, J$_{P—Rh}$=159 Hz, $^3$J$_{P—P}$=21 Hz), 37.9 (dd, J$_{P—Rh}$=160 Hz, $^3$J$_{P—P}$=21 Hz).

EXAMPLE 9

Hydrogenation of Aromatic Ketones a) Hydrogenation of Acetophenone at S/C 3000/1 in Parr™ Autoclave

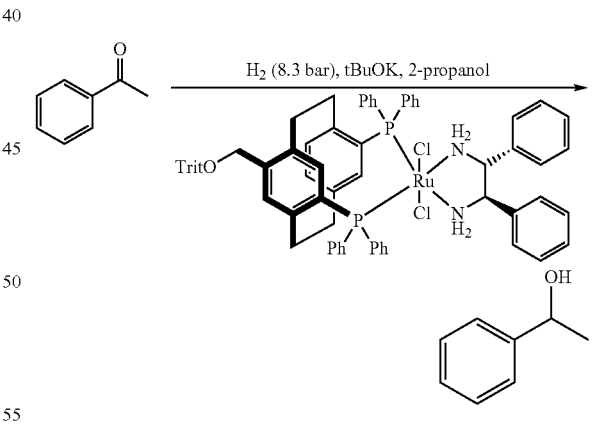

In a 50 mL glass-liner was added [(R)-TriOCH$_2$-ParaC]-RuCl$_2$-[(S,S)-Dpen] (0.002 mmol). This was placed in the Parr autoclave and the air replaced with nitrogen. A solution of acetophenone (6 mmol) and t-BuOK in 2-propanol was then added to the Parr autoclave. The Autoclave was then pressurised with hydrogen to 8.3 bar and left to stir at room temperature. After 30 minutes the uptake of hydrogen had stopped. The autoclave was opened and the solution analysed by gas-chomatography (column: Chirasil DEX-CB, method: 100° C. for 7 minutes, then 15° C. to 200° C.): >99% conversion, 98% e.e.

b) Hydrogenation of Acetophenone at S/C 5000/1 in Argonaut Endeavour™

[(R)-TrilOCH$_2$-ParaC]-RuCl$_2$-[(S,S)-Dpen] (1 mg, 0.001 mmol) was placed in a glass liner in an Argonaut multi-well pressure reactor. The vessel was purged with nitrogen and a solution of acetophenone (5 mmol) in 2-propanol (2 mL) was added. A solution of t-BuOK (0.1 mmol, B/C 100/1, 2% with respect to acetophenone) in 2-propanol (2 mL) was added, the reaction was purged with nitrogen and pressurised to 10 bar hydrogen. The pressure was maintained at 10 bar and the hydrogen uptake monitored. The reaction was complete in 40 minutes. The pressure was released and the reaction analysed by chiral gas-chromatography: >99% conversion, 98.5% e.e.

c) Example of Hydrogenation of Acetophenone at S/C 10000/1 in Parr™ Autoclave In a 50 mL glass-liner was added [(R)-TriOCH$_2$-Para-C]-RuCl$_2$-[(S,S)-Dpen] (0.001 mmol). This was placed in the Parr autoclave and the air replaced with nitrogen. A solution of acetophenone (10 mmol) and t-BuOK in 2-propanol (0.4 mmol, B/C 400, 4% with respect to acetophenone) was then added to the Parr autoclave. The Autoclave was then pressurised with hydrogen to 10 bar and left to stir at room temperature. Upon completion of the reaction, the autoclave was opened and the solution analysed by gas-chomatography (column: Chirasil DEX-CB, method: 100° C. for 7 minutes, then 15° C. to 200° C.): >99% conversion, 99% e.e.

The results for a series of catalysts are given below;

| Catalyst | S/C | Approx. time to completion | Conv. (%) | e.e. (%) |
|---|---|---|---|---|
| [(R)-TriOCH$_2$-Para-C]—RuCl$_2$—[(S,S)-Dpen] | 3000/1 | 30 min | >99 | 98 (R) |
| [(S)—MeO-Para-C]—RuCl$_2$—[(R,R)-Dpen] | 3000/1 | 30 min | >99 | 98 (S) |
| [(R)-TriOCH$_2$-Para-C]—RuCl$_2$—[(S,S)-Dpen] | 5000/1 | 40 min | >99 | 98.5 (R) |
| [(R)-TIPSOCH$_2$-Para-C]—RuCl$_2$—[(S,S)-Dpen] | 5000/1 | 15 min | >99 | 98.3 (R) |
| [(R)—HOCH$_2$-Para-C]—RuCl$_2$—[(S,S)-Dpen] | 5000/1 | 30 min | >99 | 97.9 (R) |
| [(R)-TriOCH$_2$-Para-C]—RuCl$_2$—[(S,S)-Dpen] | 10000/1 | 30 min | >99 | 99.2 (R) |
| [(R)-TIPSOCH$_2$-Para-C]—RuCl$_2$—[(S,S)-Dpen] | 10000/1 | 1 hour | >99 | 98.5 (R) |
| [(R)—HOCH$_2$-Para-C]—RuCl$_2$—[(S,S)-Dpen] | 10000/1 | 40 min | >99 | 99.3 (R) |
| [(S)—MeO-Para-C]—RuCl$_2$—[(S,S)-Dpen] | 10000/1 | 30 min | >99 | 98.6 (S) |

EXAMPLE 10

Hydrogenation of Dehydroaminoacids a) Hydrogenation of Methyl 2-acetamidoacrylate at Substrate/Catalyst=1000/1

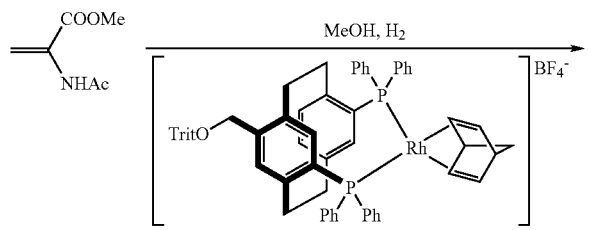

-continued

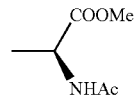

[(R)-TriOCH$_2$-ParaC Rh NBD]BF$_4$ (2.2 mg, 0.002 mmol) and methyl acetamidoacrylate (286 mg, 2 mmol) were placed in a glass liner in an Endeavour Argonaut multi-well pressure reactor. The vessel was purged with nitrogen, degassed MeOH was added (4 mL) and the reaction was pressurised to 10 bar with hydrogen. The pressure was maintained at 10 bar and the hydrogen uptake monitored. After 30 minutes the pressure was released and the reaction analysed by chiral gas-chromatography (column: Chirasil DEX-CB, method: 130° C. for 10 minutes, then 15° C./min to 200° C.): 100% conversion, 99% e.e.

b) Hydrogenation of Methyl 2-acetamidoacrylate at S/C 5000/1: General Procedure

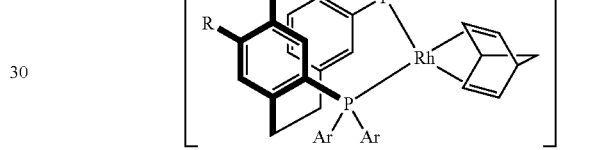

-continued

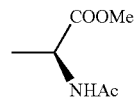

The catalyst (0.001 mmol) and methyl acetamidoacrylate (716 mg, 5 mmol) were placed in a glass liner in 50 mL Parr pressure reactor. The vessel was purged with nitrogen and then with hydrogen by pressurising to 10 bar and releasing the pressure at least three times. Degassed MeOH was added (10 mL), the reaction was purged with hydrogen as above and pressurised to 5 bar with hydrogen. The pressure was maintained between 4 and 5 bar. After 20 minutes the pressure was released and the reaction analysed by chiral gas-chromatography (column: Chirasil DEX-CB, method: 130° C. for 10 minutes, then 15° C./min to 200° C.).

The results using a series of catalysts are given below. Phanephos-based catalysts were compared with Para-C based catalysts of the present invention, demonstrating the effectiveness of the catalysts of the present invention The stereochemistry of the product was assigned according to the results reported for Phanephos-based catalysts in J. Am. Chem. Soc. 1997, 119, 6207.

| Catalyst | Approx. time to completion | Conv. (%) | e.e. (%) |
| --- | --- | --- | --- |
| [(S)-Phanephos Rh NBD]BF$_4$ | 30 min | 100 | 96.7 (S) |
| [(R)-Phanephos Rh NBD]BF$_4$ | 12 min | 100 | 96.4 (R) |
| [(R)—HO—CH$_2$-Para-C Rh NBD]BF$_4$ | 12 min | 100 | 96.8 (R) |
| [(S)-TRIO—CH$_2$-Para-C Rh NBD]BF$_4$ | 15 min | 100 | 97.0 (S) |
| [(R)-TRIO—CH$_2$-Para-C Rh NBD]BF$_4$ | 20 min | 91 | 96.5 (R) |
| [(S)-TIPSO—CH$_2$-Para-C Rh NBD]BF$_4$ | 10 min | 100 | 95.0% (S) |
| [(R)-TIPSO—CH$_2$-Para-C Rh NBD]BF$_4$ | 12 min | 100 | 96.2 (R) |
| [rac-CH$_3$O-Para-C Rh NBD]BF$_4$ | 15 min | 100 | NA |
| [(S)—CH$_3$O-Para-C Rh NBD]BF$_4$ | 20 min | 100 | 96.0 (S) |
| [(R)—CH$_3$O-Para-C Rh NBD]BF$_4$ | 8 min | 100 | 96.7 (R) |
| [rac-TBSO-Para-C Rh NBD]BF$_4$ | 8 min | 100 | NA |
| [(S)-Xyl-Phanephos Rh NBD]BF$_4$ | <10 min | 100 | 97.9 (S) |
| [(S)-TIPSO—CH$_2$-Xyl-Para-C Rh NBD]BF$_4$ | 5 min | 100 | 97.2 (S) |
| [(S)—MeOXyl-Phanephos Rh NBD]BF$_4$ | 5 min | 100 | 98.0 (S) |
| [(S)—HO—CH$_2$—MeOXyl-Para-C Rh NBD]BF$_4$ | 20 min | 100 | 95.0 (S) |

NA = Not Analysed

The invention claimed is:

1. A substituted paracyclophane of formula (I)

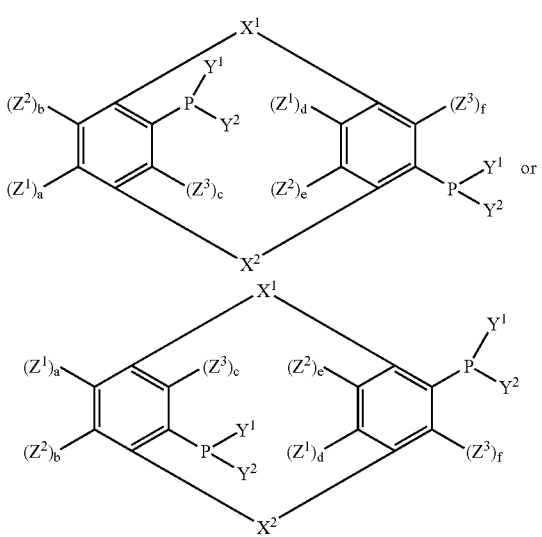

wherein $X^1$ and $X^2$ are linking groups comprising between 2 to 4 carbon atoms, $Y^1$ and $Y^2$ are selected from the group consisting of hydrogen, halide, oxygen, nitrogen, alkyl, cycloalkyl, aryl and heteroaryl, and $Z^1$, $Z^2$ and $Z^3$ are substituting groups selected from the group consisting of:
  (i) C1-C30 branched or linear alkyl, aryl, aralkyl or alkaryl groups,
  (ii) functional groups selected from the group consisting of halide, hydroxyl, alkoxy, carbonyl, carboxyl, anhydride, methacryl, epoxide, vinyl, nitrile, nitro, sulphate, sulphonyl, silyl, mercapto, amino, amine, imine, amide and imide, and
  (iii) C1-C30 branched or linear alkyl, aryl, aralkyl or alkaryl groups bearing thereon one or more of said functional groups, wherein —a, b, c, d, e and f are 0 or 1, and (a+b+c+d+e+f)=1 to 6.

2. A substituted paracyclophane according to claim 1 wherein $X^1$ and $X^2$ are both —C$_2$H$_4$—.

3. A substituted paracyclophane according to claim 1 wherein $Z^1$, $Z^2$ and $Z^3$ are substituting groups selected from the group consisting of —CH$_3$ (ME), —C(CH$_3$)$_3$ (tBu), —CH(CH$_3$)$_2$ (iPr), —C$_5$H$_5$ (Ph); fluoroalkyl groups of formula —C$_x$H$_y$F$_z$ (where x is 1 to 10, y is less than 2x, including 0; and z=1 to 2x+1). Vinyl —CH═CH$_2$, iodide —I, nitrate —NO$_2$, —N═CPh$_2$, alkoxymethylene or alkoxy groups of formulae R'OCH$_2$— or R'O— (where R'=H, alkyl C1-C30, aryl, alkaryl or silyl); carbonyl XC(O)— (where X=H, halide, or alkyl C1-C30), carboxyl R"OC— (where R"=H, alkyl C1-C30, aryl or alkaryl); and amino R'R"N—, R'R"NCH$_2$— or R'R"NCO— (where R' and/or R"=H, alkyl, or alkaryl).

4. A substituted paracyclophane according to claim 1 wherein one or both of the benzene rings in the paracyclophane bears a substituting group in the para ($Z^1$) position to the P($Y^1Y^2$) group.

5. A substituted paracyclophane according to claim 1 wherein (a+b+c+d+e+f)=1 or 2.

6. A substituted paracyclophane according to claim 1 wherein (a+b+c)=1 or (d+e+f)=1, or both of these.

7. A method for preparation of a substituted paracyclophane of (I) by,

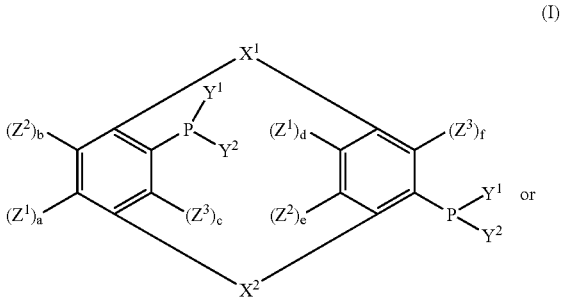

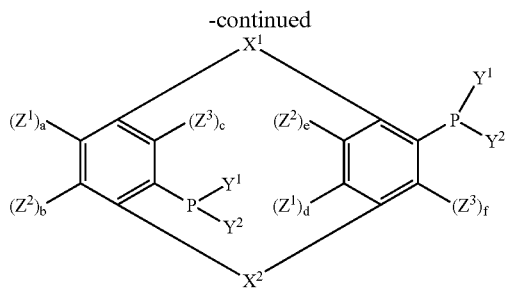

(a) performing a substitution reaction on a pseudo-ortho dibromoparacyclophane to form an Intermediate substituted pseudo-ortho dibromoparacyclophane of formula (II), and

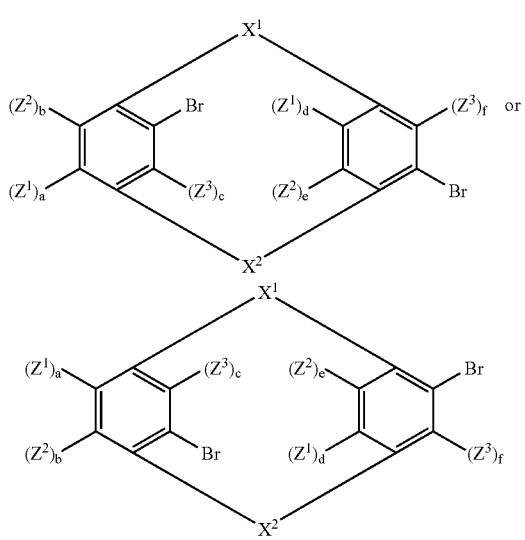

(b) reacting the-substituted pseudo-ortho dibromoparacyclophane with a phosphorus compound comprising P(Y$^1$Y$^2$), wherein X$^1$ and X$^2$ are linking groups comprising between 2 to 4 carbon atoms, Y$^1$ and Y$^2$ are selected from the group consisting of hydrogen, halide, oxygen, nitrogen, alkyl, cycloalkyl, aryl and heteroaryl, and Z$^1$, Z$^2$ and Z$^3$ are substituting groups selected from the group consisting of:

(i) C1-C30 branched or linear alkyl, aryl, aralkyl, or alkaryl groups, (ii) functional groups selected from the group consisting of halide, hydroxyl, alkoxy, carbonyl, carboxyl, anhydride, methacryl, epoxide, vinyl, nitrile, nitro, sulphate, sulphonyl, silyl, mercapto, amino, amine, imine, amide and imide, and (iii) C1-C30 branched or linear alkyl, aryl, aralkyl or alkaryl groups bearing thereon one or more of said functional groups, wherein a, b, c, d, e and f are 0 or 1, and (a+b+c+d+e+f)=1 to 6.

8. A method according to claim 7 wherein the substitution reaction is a Lewis-acid mediated electrophilic substitution.

9. A substituted pseudo-ortho dibromoparacyclophane of formula (III)

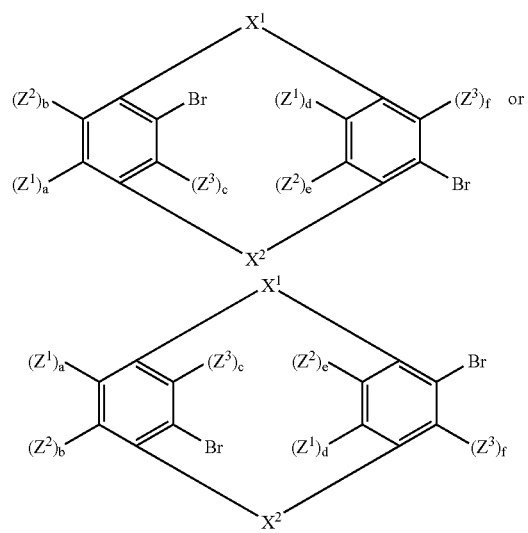

wherein X$^1$ and X$^2$ are linking groups comprising between 2 to 4 carbon atoms, Z$^1$, Z$^2$ and Z$^3$ are substituting groups at least one of which comprises a functional group selected from the group consisting of hydroxyl, alkoxy, carboxyl, anhydride, methacryl, epoxide, vinyl, nitrile, nitro, sulphate, sulphonyl, mercapto, sulphide amino, amine, imine, and imide, a, b, c, d, e and f are 0 or 1, and (a+b+c+d+e+f)=1 to 6.

10. A substituted pseudo-ortho dibromoparacyclophane according to claim 9 wherein the functional group is a carboxylic acid functional group or an amino functional group.

11. A metal complex comprising the reaction product or a metal compound and a substituted paracyclophane of formula (I)

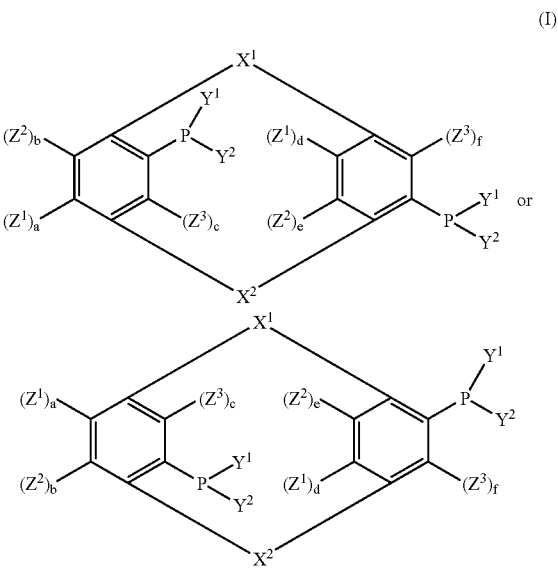

wherein X$^1$ and X$^2$ are linking groups comprising between 2 to 4 carbon atoms, Y$^1$ and Y$^2$ are selected from the group consisting of hydrogen, halide, oxygen, nitrogen, alkyl, cycloalkyl, aryl and heteroaryl, and $Z^1$, $Z^2$ and $Z^3$ are substituting groups selected from the group consisting of:
  (i) C1-C30 branched or linear alkyl, aryl, aralkyl or alkaryl groups,
  (ii) functional groups selected from the group consisting of halide, hydroxyl, alkoxy, carbonyl, carboxyl, anhydride, methacryl, epoxide, vinyl, nitrile, nitro, sulphate, sulphonyl, silyl, mercapto, amino, amine, imine, amide and imide, and
  (iii) C1-C30 branched or linear alkyl, aryl, aralkyl or alkaryl groups bearing thereon one or more of said functional groups,
wherein a, b, c, d, e and f are 0 or 1, and (a+b+c+d+e+f)=1 to 6.

12. A metal complex according to claim 11 wherein the metal compound is a compound of palladium (Pd), platinum (Pt), rhodium (Rh), Iridium (Ir) or ruthenium (Ru).

13. A metal complex according to claim 11 wherein the substituted paracyclophane (I) is substantially enantiomerically-pure.

14. A metal complex according to claim 11 wherein the metal complex is supported on a solid support.

15. A method of asymmetrically hydrogenating a substrate comprising contacting the substrate with hydrogen in the presence of a catalytic amount of a metal complex according to claim 12.

16. A method of catalysing a chemical reaction, the method comprising contacting one or more reactants with a metal complex according to claim 12, wherein the chemical reaction is selected from the group consisting of carbon-carbon coupling reactions, the enantioselective isomerization of olefins, asymmetric hydroboration reactions, asymmetric cyclisation of olefinic aldehydes, asymmetric arylation reactions, asymmetric alkylation reactions, and aminations of aryl halides according to the Hartwig-Buchwald reaction.

* * * * *

UNITED STATES PATENT AND TRADEMARK OFFICE
CERTIFICATE OF CORRECTION

PATENT NO. : 7,256,302 B2  Page 1 of 1
APPLICATION NO. : 10/560387
DATED : August 14, 2007
INVENTOR(S) : Beatriz Dominguez et al.

It is certified that error appears in the above-identified patent and that said Letters Patent is hereby corrected as shown below:

At column 44, line 31, "(ME)" should read -- (Me) --.

At column 44, line 32, "-$C_5H_5$" should read -- -$C_6H_5$ --.

At column 44, line 33, "-$C_xH_yF_2$" should read -- -$C_xH_yF_z$ --.

At column 46, line 38, "the reaction product or a" should read -- the reaction product of a --.

At column 44, line 53, "of (I)" should read -- of formula (I) --.

Signed and Sealed this

First Day of July, 2008

JON W. DUDAS
*Director of the United States Patent and Trademark Office*